(12) United States Patent
Lunner et al.

(10) Patent No.: US 10,362,414 B2
(45) Date of Patent: Jul. 23, 2019

(54) HEARING ASSISTANCE SYSTEM COMPRISING AN EEG-RECORDING AND ANALYSIS SYSTEM

(71) Applicant: Oticon A/S, Smørum (DK)

(72) Inventors: Thomas Lunner, Smørum (DK); Fredrik Gustafsson, Linköping (SE); Carina Graversen, Smørum (DK); Emina Alickovic, Linköping (SE)

(73) Assignee: OTICON A/S, Smørum (DK)

( * ) Notice: Subject to any disclaimer, the term of this patent is extended or adjusted under 35 U.S.C. 154(b) by 37 days.

(21) Appl. No.: 15/645,606

(22) Filed: Jul. 10, 2017

(65) Prior Publication Data

US 2018/0014130 A1 Jan. 11, 2018

(30) Foreign Application Priority Data

Jul. 8, 2016 (EP) .................................. 16178536

(51) Int. Cl.
*H04R 25/00* (2006.01)
*A61N 1/36* (2006.01)
(Continued)

(52) U.S. Cl.
CPC ......... *H04R 25/402* (2013.01); *A61B 5/0476* (2013.01); *A61F 11/06* (2013.01);
(Continued)

(58) Field of Classification Search
CPC .. H04R 1/1091; H04R 25/505; H04R 25/558; H04R 2225/55; H04R 25/55;
(Continued)

(56) References Cited

U.S. PATENT DOCUMENTS 9,712,931 B2 * 7/2017 Adachi ............. A61B 5/04845
2014/0098981 A1 4/2014 Lunner et al.
2016/0099008 A1 4/2016 Barker et al.

FOREIGN PATENT DOCUMENTS

EP 2 560 412 A1 2/2013
EP 2560412 * 8/2013 ............. H04R 25/00
EP 2 997 893 A1 3/2016

OTHER PUBLICATIONS

Mattias Tiger, "Sparse Linear Modeling of Speech from EEG", Jan. 1, 2014, Linkoping, Sweden.*

(Continued)

*Primary Examiner* — Amir H Etesam
(74) *Attorney, Agent, or Firm* — Birch, Stewart, Kolasch & Birch, LLP

(57) ABSTRACT

A hearing assistance system comprises an input unit for providing electric input sound signals $u_i$, each representing sound signals $U_i$ from a multitude $n_u$ of sound sources $S_i$, an electroencephalography (EEG) system for recording activity of the auditory system of the user's brain and providing a multitude $n_y$ of EEG signals $y_j$, and a source selection processing unit receiving said electric input sound signals $u_i$ and said EEG signals $y_j$, and in dependence thereof configured to provide a source selection signal $\hat{S}_x$ indicative of the sound source $S_x$ that the user currently pays attention to using a selective algorithm that determines a sparse model to select the most relevant EEG electrodes and time intervals based on minimizing a cost function measuring the correlation between the individual sound sources and the EEG signals, and to determine the source selection signal $\hat{S}_x$ based on the cost functions obtained for said multitude of sound sources.

17 Claims, 10 Drawing Sheets

(51) Int. Cl.
    *A61B 5/0476*     (2006.01)
    *A61F 11/06*       (2006.01)
    *H04R 1/10*        (2006.01)

(52) U.S. Cl.
    CPC ....... *A61N 1/36038* (2017.08); *H04R 1/1041* (2013.01); *H04R 25/407* (2013.01); *H04R 25/505* (2013.01); *H04R 25/554* (2013.01); *H04R 25/552* (2013.01); *H04R 2225/43* (2013.01); *H04R 2225/61* (2013.01); *H04R 2225/67* (2013.01)

(58) Field of Classification Search
    CPC .... H04R 25/50; H04R 5/0335; H04R 25/554; H04R 25/70; H04R 25/552; H04R 3/005; H04R 25/305
    See application file for complete search history.

(56) References Cited

OTHER PUBLICATIONS

Alickovic et al., "A sparse estimation approach to modeling listening attention from EEG signals", to be published.
Tiger, "Sparse Linear Modeling of Speech from EEG", Jan. 1, 2014, XP055336334, Linkoping, Sweden, Retrieved from the Internet: URL:http://www.diva-portal.org/smash/get/diva2:728869/FULLTEXT01.pdf, Retrieved Jan. 18, 2017. Paragraphs [01.3]-[01.5], [0006].

* cited by examiner

HEARING ASSISTANCE SYSTEM COMPRISING AN EEG-RECORDING AND ANALYSIS SYSTEM

SUMMARY

The present application deals with hearing assistance systems, e.g. comprising one or more hearing aids. The disclosure deals in particular with the problems encountered by a (normally hearing or hearing impaired) user in an acoustic environment comprising a multitude of sound sources ('competing sounds'). The disclosure relates specifically to the problem of identifying which of the multitude of current sound sources that the user is interested in listening to.

An important issue in connection with automatic sound source location using brainwave signals, is the processing unit's ability to identify (and focus on) relevant EEG channels and relevant time spans (where signals e.g. reflect potentials evoked by sound).

According to embodiments of the present disclosure, it is proposed to use a sparse model to solve the problem. It should be noted, however, that a sparse model can be useful for other purposes that the pure selection of a single sound source that the user is (assumed to be) attending to. For instance, to determine if the user attends to a single sound source or not. A 'sparse model' (or 'sparse machine learning') is a term from the field of machine learning. The 'sparsity' indicates that the method suitable for applications with a limited computational capacity, such as in portable devices, e.g. hearing aids. Sparse machine learning methods aim at making a compromise between fitting perfection and sparsity of the results (with a view to ease of interpretation, cf. e.g. parameter $\lambda$ in eq. (10) (or (6)') below). An example of a sparse machine learning method is e.g. provided by a variant of the least squares method termed the 'least absolute shrinkage and selection operator' (LASSO) involving classification and regression, cf. e.g. reference [26].

A benefit of embodiments of the scheme according to the present disclosure is the sparse structure, and an advantage of embodiments of the disclosure is that electrodes and time intervals producing pure noise (uncorrelated with sound sources) may be excluded from the decision model, and that the sparse model requires less computational resources and energy.

A Hearing Assistance System:

In a first aspect of the present application, a hearing assistance system is provided. The hearing assistance system comprises an input unit for providing electric input sound signals $u_i$, each representing sound signals $U_i$ from a multitude $n_u$ of sound sources $S_i$ ($i=1, \ldots, n_u$), an electroencephalography (EEG) system for recording activity of the auditory system of the user's brain and providing a multitude $n_y$ of EEG signals $y_j$ ($j=1, \ldots, n_y$), and a source selection processing unit coupled to said input unit and to said EEG-system and receiving said electric input sound signals $u_i$ and said EEG signals $y_j$, and in dependence thereof configured to provide a source selection signal $\hat{S}_x$ indicative of the sound source $S_x$ that the user currently pays attention to.

The source selection processing unit is configured to analyze said electric input sound signals $u_i$, $i=1, \ldots, n_u$, and said multitude of EEG signals $y_j$, $j=1, \ldots, n_y$, use a selective algorithm that determines a sparse model to select the most relevant EEG electrodes and time intervals based on minimizing a cost function measuring the correlation between the (individual) sound source and the EEG signals, and to determine the source selection signal $\hat{S}_x$ indicative of the sound source $S_x$ that the user currently (mainly) pays attention to based on the cost functions obtained for said multitude of sound sources.

In a second aspect of the present application, a hearing assistance system is provided. The hearing assistance system comprises an input unit for providing electric input sound signals $u_i$, each representing sound signals $U_i$ from a multitude $n_u$ of sound sources $S_i$ ($i=1, \ldots, n_u$), an electroencephalography (EEG) system for recording activity of the auditory system of the user's brain and providing a multitude $n_y$ of EEG signals $y_j$ ($j=1, \ldots, n_y$), and a source selection processing unit coupled to said input unit and to said EEG-system and receiving said electric input sound signals $u_i$ and said EEG signals $y_j$, and in dependence thereof configured to provide a source selection signal $\hat{S}_x$ indicative of the sound source $S_x$ that the user currently pays attention to The source selection processing unit is configured to analyze said electric input sound signals $u_i$, $i=1, \ldots, n_u$, and said multitude of EEG signals $y_j$, $j=1, \ldots, n_y$, determine a dynamic finite impulse response (FIR) filter from each sound source to each EEG channel, and to determine the source selection signal $\hat{S}_x$ indicative of the sound source $S_x$ that the user currently (mainly) pays attention to based on cost functions obtained for said multitude of sound sources.

Thereby an improved hearing assistance system may be provided.

In an embodiment the source selection processing unit is configured to determine a dynamic finite impulse response (FIR) filter from each sound source to each EEG channel in that a causal model, described by the FIR filter, is determined. The individual causal models are configured to determine each of the $n_y$ EEG signals ($y_j$, $j=1, \ldots, n_y$) from the $n_u$ sound source signals (or electric input signals $u_i$, $i=1, \ldots, n_u$), cf. e.g. eq. (2) below.

The hearing assistance system, or at least parts thereof, is preferably adapted to be portable, e.g. body-worn, e.g. embodied in one or more devices attached to the head of a user and/or otherwise worn by or carried by the user. Preferably, the EEG system for recording activity of the auditory system of the user's brain is adapted to be fully or partially worn on the head of the user, e.g. fully or partially at or in the ears of the user, or fully or partially implanted in the head of the user. In an embodiment, the input unit, or at least parts thereof, e.g. one or more input transducers (e.g. microphones), is adapted to be portable, e.g. body-worn, e.g. to be fully or partially worn on the head of the user, e.g. fully or partially at or in the ears of the user, or fully or partially implanted in the head of the user.

In an embodiment, the source selection processing unit is configured to determine a dynamic finite impulse response (FIR) filter from each sound source to each EEG channel. In a first step (e.g. executed prior to ordinary use of the hearing assistance system), the active taps in the sparse FIR filter are estimated for the user in question. This has the advantage of providing a (prior) space-time resolution of which EEG channels that reveal information about listening attention (for the given EEG sensor configuration), and the delays and time intervals the brain uses to process (e.g. speech) sound. In a second step (e.g. executed during ordinary use of the hearing assistance system), the source selection processing unit is configured to use the estimated sparse FIR filter (in a real-time implementation) to determine which of two (or more) competing sound sources that the user is currently attending to.

An advantage of the approach according to the present disclosure is the sparse structure. A further advantage is that electrodes and time intervals producing pure noise (uncorrelated with sound sources) may be excluded from the decision model. A further advantage of embodiments of the disclosure is that the sparse model may require less computational resources and energy, which is of importance in portable device (relying on a local energy source, e.g. a battery).

The linear finite impulse filter (FIR) is defined by parameters $b_{ij}(t)$, where t represents time. In an embodiment, it is assumed that a causal relation between sound stimuli $u_i(t)$ (i=1, 2, . . . , $n_u$) and the EEG signals $y_j(t)$ (j=1, 2, . . . , $n_y$) can be modeled by a the linear finite impulse filter (FIR). In an embodiment, the dynamics of the causal relation is modeled as the convolution (e.g. moving average, weighted average)

$$y_j(t) = b_{ij} * u_i(t) + e_j(t) = \sum_{k=1}^{n_b} b_{ij}(k) u_i(t-k) + e_j(t)$$

where $n_b$ is the model order (design parameter) of the FIR filter, and where $e_j(t)$ is the disturbance, and k is a model order index, e.g. k=1, . . . , $n_b$, e.g. 1≤k≤256.

In an embodiment, comprising N samples of $u_i(t)$ and $y_j(t)$, the causal relation (2) can be written in vector form as $$Y_j = \mathcal{H}(U_i) B_{ij} + E_j$$

where $Y_j=(y_j(1), \ldots, y_j(N))^T$ and similarly for U and E, while $B_{ij}=(b_{ij}(1), \ldots, b_{ij}(n_b))^T$ and $\mathcal{H}(U_i)$ is a Hankel matrix with elements $\mathcal{H}(U_i)^{mn}=u_j(m-n)$.

In an embodiment, the least squares (LS) method estimates the FIR parameters by the minimizing argument (arg min) of the two norm of the estimation error $$\hat{B}_{ij} = \underset{B}{\operatorname{argmin}} V_{ij}(B)$$

$$\hat{B}_{ij} = \underset{B}{\operatorname{argmin}} \|Y_j - \mathcal{H}(U_i) B_{ij}\|_2^2$$

$$\hat{B}_{ij} = \mathcal{H}(U_i)^\dagger Y_j$$

where $\mathcal{H}(U_i)^\dagger = (\mathcal{H}(U_i)^T \mathcal{H}(U_i))^T \mathcal{H}(U_i)^T$ denotes the pseudo inverse.

In an embodiment, the source selection processing unit is configured to use a stimuli reconstruction (SR) method for estimating the FIR inverse model from EEG signal to sound source, e.g.

$$u_i(t) = a_{ij} * y_j(t) + v_i(t) = \sum_{k=1}^{n_a} a_{ij}(k) y_j(t+k) + v_i(t)$$

$$U_i = \mathcal{H}(Y_i) A_{ij} + V_i$$

where the linear finite impulse filter (FIR) of the inverse model is defined by parameters $a_{ij}(t)$, where $n_a$ is a model order of the FIR filter, and where $v_i(t)$ is the disturbance (loss/cost).

In an embodiment, the source selection processing unit is configured to classify the attended source $\hat{i}$ using arg $\min_i$ $V_{ij}(\hat{B}_{ij})$, that is, the sound source that best explains the EEG signal (e.g. $\hat{i}$=arg $\min_i$ $V_{ij}(\hat{B}_{ij})$), where $V_{ij}(\hat{B}_{ij})$ is the loss (or cost) function.

In an embodiment, the source selection processing unit is configured to use a sparse model for modeling the sound sources. In an embodiment, source selection processing unit is configured to use the cost function $$V_i(B) = \sum_{j=1}^{n_y} \|Y_j - \mathcal{H}(U_i) B_j\|_2^2 + \lambda \|(B_1, B_2, \ldots, B_{n_y})\|_1$$

where the first term, indicated by subscript 2, represents a $l_2$ regularization, and the second term, indicated by subscript 1, represents a $l_1$ regularization, B is the total multiple output FIR filter $B=(B_1, B_2, \ldots, B_{n_y})$ for input i, the parameter $\lambda$ is used to compromise sparseness to model fit, and the $l_1$ regularization term is an approximation of the $l_0$ norm that simply counts the number of non-zero elements in the FIR filter B. Thereby, a compromise between a good model fit and a sparse FIR filter with few parameters is provided. The $l_1$ norm is used to get a convex problem, where efficient numerical solvers can be used.

In an embodiment, the source selection processing unit is configured to use the alternating direction method of multipliers (ADMM) methodology to reformulate the optimization problem into another one with a different (adapted to the ADMM methodology) cost function (e.g. with different B vectors in the cost function). In an embodiment, the cost function $V_i(B)$ is subject the equality constraint, $$V_i(B) = \sum_{j=1}^{n_y} \|Y_j - \mathcal{H}(U_i) B_j\|_2^2 + \lambda \|\bar{B}\|_1$$

subject to $\bar{B} = B$.

An advantage thereof is that it provides a more efficient method (provides fast convergence in only a few iterations).

The alternating direction method of multipliers (ADMM) is an algorithm aimed at optimization problems. The algorithm has its origin in statistics and machine learning. The strategy of the ADMM is to divide a convex optimization problem into a number of separate (smaller) problems, which are (individually) less complex, and thus appropriate for systems having limited computational resources (e.g. portable devices, such as hearing aids). The ADMM is e.g. discussed in detail in [4].

In an embodiment, the source selection processing unit is configured to analyze said electric input sound signals $u_i$, i= 1, . . . , $n_u$, and said multitude of EEG signals $y_j$, j=1, . . . , $n_y$, based on
 a full FIR single input multiple output (SIMO) model for each electric input sound signal based on said electric input sound signals $u_i$ and said EEG signals $y_j$,
 an alternating direction method of multipliers (ADMM) to provide sparse models from said full FIR single input multiple output (SIMO) models for use in identifying the model that best describes the corresponding electric input sound signal and EEG signal data,
wherein the sound source $S_x$ that the user currently pays attention to is determined by comparing cost functions of each model.

In an embodiment, the source selection processing unit is configured to provide that the sound source $S_x$ that the user currently pays attention to is determined by comparing the moving average (MA) of cost functions of each model (e.g. identifying the sound source that provides a minimum cost function).

In an embodiment, an LS (least squares) estimation for each FIR SIMO model in eq. (10)' below is performed and the input $U_i$ signal which gives the smallest cost is determined. In an embodiment a cost function for the i-th input signal $U_i$ and the model parameters $B_i$ for the n-th batch can be expressed as $$\hat{V}_N^i(n) = \tfrac{1}{2}\|Y - U_i B_i\|^2 + \lambda \|\underline{B}_i\|_1$$

where Y is a data matrix containing EEG signals with dimension $N \times n_y$ (N is the number of measurements and $n_y$ is the number of EEG electrodes), $U_i$ is a data matrix containing the i-th electric input sound signal with dimension $N \times k$, where k is the number of time lags included in the model, $B_i$ is a matrix containing the impulse responses with dimension $k \times n_y$, $\lambda$ is the regularizer, and $\lambda \leq 0$, and $\|\cdot\|$ denotes the Frobenius norm of the residual, and $\|\cdot\|_1$ denotes the $l_1$ norm, and the n-th batch refers to n-th epoch for which we intend to identify the sound source of the listener's interest. In an embodiment, the sound source attended to by the user is determined as $$\hat{i} = \arg\min_i \hat{V}_N^i(n).$$

In an embodiment, the sound source $\hat{i}$ attended to by the user is determined based on a moving average (MA(p)) of the loss (cost) functions:

$$\hat{V}_{MA}^i(k) = \sum_{i=0}^{p-1} \hat{V}_N^i(n-i)$$

$$\hat{i} = \arg\min_i \hat{V}_{MA}^i(k),$$

where the index k is the model order of the FIR model.

In an embodiment, the input unit comprises a number of receivers, e.g. wireless receivers, for receiving at least some, such as a majority or all of, said electric input sound signals $u_i$, each representing sound signals $U_i$ from a multitude n of sound sources $S_i$ (i=1, ..., $n_u$). In an embodiment, the electric input sound signals $u_i$ represent sound picked up by respective microphones, e.g. worn by respective speakers. In an embodiment, the electric input sound signals $u_i$ represent streamed sound received from respective media.

In an embodiment, the input unit comprises a sound source separation unit for providing said electric input sound signals $u_i$, from one or more electric input sound signals representative of a mixture of said sound signals $U_i$. One or more electric input sound signals $u_{total,m}$, m=1, ..., M, representative of a mixture of said sound signals $U_i$, may e.g. be provided by one or more input transducers (e.g. microphones) of the hearing system, e.g. of a hearing device located at an ear of the user, or of a pair hearing devices located at left and right ears of the user.

In an embodiment, the hearing assistance system (e.g. comprising one or more (e.g. two) hearing devices) comprises a distributed microphone system (comprising a multitude of microphones that interact to resolve an auditory scene). In an embodiment, the hearing assistance system comprises a speakerphone (comprising a number of input transducers and a number of output transducers, e.g. for use in an audio conference situation), e.g. comprising a beamformer filtering unit, e.g. providing multiple beamforming capabilities.

In an embodiment, the hearing assistance system is configured to provide an estimate $\hat{u}_x$ of the sound signal $U_x$ that the user currently pays attention to. In general, the estimate $\hat{u}_x$ of the sound signal $U_x$ that the user currently pays attention to comprises one of the electric input sound signals $u_i$, i=1, ..., $n_u$. In an embodiment, $\hat{u}_x$ is equal to one of the electric inputs sound signals $u_i$. In an embodiment, $\hat{u}_x$ is a modified (e.g. amplified and/or frequency shaped) version of one of the electric input sound signals $u_i$. In an embodiment, $\hat{u}_x$ is a weighted combination of the electric input sound signals $u_i$ ($\hat{u}_x = w_1 \cdot u_1 + \ldots + w_{nu} \cdot u_{nu}$, where $\Sigma_i w_i = 1$). In an embodiment, the weights are determined by the source selection processing unit, according to the cost functions (e.g. in that the larger a value of the cost function for a given signal $u_i$ is, the lower is the weight $w_i$ for that signal), optionally giving a fixed weight (e.g. 0.75) to the electric inputs sound signal $u_x$ that the user currently is assumed to pay attention to).

In an embodiment, the EEG system comprises a multitude of EEG sensors for providing said multitude of EEG signals $y_j$ (i=1, ..., $n_y$). In an embodiment, one or more of the EEG sensors, such as each EEG sensor, comprises an EEG-electrode. In an embodiment, the EEG system comprises an electrical potential sensor for sensing an electrical potential, and electronic circuitry coupled to the electrical potential sensor to provide an amplified output. In another embodiment, the EEG system comprises a magnetic field sensor for sensing a magnetic field, and electronic circuitry coupled to the magnetic field sensor to provide an amplified output. In an embodiment, the electrical potential and/or magnetic field sensors are configured to sense electric and/or magnetic brain wave signals, respectively. In an embodiment, the EEG system comprises a sensor configured to be capacitively or inductively coupled to the surface of the user's head, when the EEG system is operatively mounted on the user. In an embodiment, the number of EEG sensors (or EEG electrodes) is larger than 2, such as larger than 4, such as larger than 10, such as larger than 25. In an embodiment, the number of EEG sensors (or EEG electrodes) is in the range from 2 to 200, such as in the range from 2 to 25, e.g. in the range from 2 to 10.

In an embodiment, the hearing assistance system comprises one or two hearing devices, each hearing device being adapted for being located at or in an ear or for being fully or partially implanted in the head of a user, the or each hearing device comprising an output unit for providing output stimuli perceivable by the user as sound, based on said estimate $\hat{u}_x$ of the sound signal $U_x$ that the user currently pays attention to. In an embodiment, the hearing assistance system is configured to provide said estimate $\hat{u}_x$ as a weighted combination of said electric input sound signals $u_i$, i=1, ..., $n_u$, to the output unit(s). In an embodiment, the weights $w_i$, i=1, ..., $n_u$, are determined by the sound selection processing unit, e.g. by comparing cost functions of each model and ranking the costs ($\hat{u}_x = \Sigma_i (w_i \cdot u_i)$ (where the summation is over i=1, ..., $n_u$)). In an embodiment, the sum of the weights $w_i$ over i=1, ..., $n_u$ is 1. In an embodiment, the weight $w_x$ for the electric input sound signal $u_x$ corresponding to the sound source $S_x$ that the user currently pays attention to is larger than 0.5, such as larger than 0.7, such as larger than 0.85.

In an embodiment, the hearing device(s) comprise(s), at least a part, such as all of, said input unit. In an embodiment, the input unit is shared between first and second hearing devices of the hearing assistance system. In an embodiment, the input unit is divided in separate input sub-units of the first and second hearing devices of the hearing assistance system, each of the first and second hearing devices providing output stimuli perceivable by the user as sound, based on estimates $\hat{u}_{x1}$ and $\hat{u}_{x2}$, respectively, of the sound signal $U_x$ that the user currently pays attention to. In an embodiment, each of the first and second hearing devices comprises an independent source selection processing unit, allowing output stimuli perceivable by the user as sound to be provided based on independent estimates $\hat{u}_{x1}$ and $\hat{u}_{x2}$, respectively, of the sound signal $U_x$ that the user currently pays attention to.

In an embodiment, the hearing device(s) comprise(s) at least a part of said EEG system, such as at least some of said EEG-electrodes. In an embodiment, at least some of the electrodes are included in the hearing device(s). In an embodiment, a majority, such as all of the EEG-sensors are included in the hearing device(s). In an embodiment, (only) a reference electrode is external to the hearing device(s). In an embodiment, the EEG-system form part of the hearing device(s), e.g. including a reference electrode.

In an embodiment, the hearing assistance system comprises first and second hearing devices, wherein the hearing assistance system is configured to allow the exchange of information between the first and second hearing devices and/or between the first and second hearing devices and an auxiliary device. In an embodiment, the first and second hearing devices comprises antenna and transceiver circuitry allowing the exchange of electric input sound signals $u_{i1}$ and $u_{i2}$ provided by the respective input units of the first and second hearing devices, respectively, (or signals originating therefrom) between the two hearing devices and/or with an auxiliary device. In an embodiment, the first and second hearing devices are configured to exchange EEG signals $y_{j1,1}$ and $y_{j2,2}$ provided by the EEG-systems of the first and second hearing devices, respectively, (or signals originating therefrom), and/or to provide the respective EEG signals to an auxiliary device. Indices j1 and j2 refer to EEG signals picked up by the respective first and second hearing devices, where j1=1, . . . , $n_{y1}$, and j2=1, . . . , $n_{y2}$, respectively, and $n_{y1}+n_{y2} \leq n_y$.

In an embodiment, the hearing assistance system is configured to include the electric input sound signals $u_{i,1}$ and $u_{i,2}$ provided by the respective input units, and/or the EEG signals $y_{j1,1}$ and $y_{j2,2}$ provided by the respective EEG-systems of the first and second hearing devices in the determination of the sound source $S_x$ that the user currently pays attention to.

In an embodiment, the hearing assistance system comprises an auxiliary device configured to exchange information with the hearing device or with the first and second hearing devices. In an embodiment, the hearing assistance system is configured to transmit said electric input sound signals and/or said EEG signals to the auxiliary device. In an embodiment, the auxiliary device comprises said source selection processing unit coupled to said input unit and to said EEG-system, and is configured to provide a source selection signal indicative of the sound source $S_x$ that the user currently pays attention to. In an embodiment, the auxiliary device is configured to provide the electric sound signal u representing the sound source $S_x$ that the user currently pays attention to.

In an embodiment, the hearing assistance system is configured to maintain or apply appropriate directional cues for the electric sound signal $u_x$ representing the sound source $S_x$ that the user currently pays attention to. In an embodiment, the hearing assistance system (e.g. the auxiliary device or the first and second hearing devices) is configured to maintain time and level difference between the received electric input sound signals $u_x$ of the first and second hearing devices in the electric sound signals $\hat{u}_{x,1}$ and $\hat{u}_{x,2}$, representing the sound source $S_x$ that the user currently pays attention to, presented to the user (so that directional cues are maintained). In an embodiment, the hearing assistance system (e.g. the auxiliary device or the first and second hearing devices) is configured to apply appropriate head related transfer functions (HRTF) to the electric sound signals $\hat{u}_{x,1}$, and $\hat{u}_{x,2}$, representing the sound source $S_x$ that the user currently pays attention to, and which are presented to the user by the first and second hearing devices, respectively (so that directional cues are maintained). The head related transfer functions may e.g. be available in a database accessible to (e.g. stored in) the first and second hearing device and/or to the auxiliary device. Relevant HRTFs in a given situation may e.g. be determined from knowledge of the corresponding electric input sound signals $u_{i,1}$ and $u_{i,2}$ received by the first and second hearing devices, respectively, at a given point in time (e.g. level and/or phase).

In an aspect of the present disclosure, the output of two attention analyses (for example based on FIR models and/or ADMM as described in the present disclosure) is used to compare if a hearing aid signal processing increases (or decreases) the loss function of attended versus unattended signals. The first analysis is preferably done without the hearing aid signal processing to determine the reference loss functions for attended and unattended signals. In the second analysis a hearing aid signal processing is added on the attended target and the unattended target signal. The differences in loss function between the first and the second analysis determine the hearing aid signal processing effect (outcome measure). In other words, an 'outcome measure' for estimating the effect of the hearing aid processing to compensate for a hearing impairment can thereby be determined.

In an embodiment, the hearing device or devices comprises a hearing aid, a headset, an earphone, an ear protection device or a combination thereof.

In an embodiment, the hearing assistance system (e.g. the hearing device or devices) comprises a multi-input beamformer filtering unit for providing a weighted combination of a multitude M of electric input sound signals $IN_m$, m=1, . . . , M, each electric input sound signal representing a mixture of said sound signals $U_i$.

In an embodiment, the hearing assistance system is adapted to establish a communication link between the hearing device and the auxiliary device to provide that information (e.g. control and status signals, possibly audio signals) can be exchanged or forwarded from one to the other.

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for allowing selecting and/or combining an appropriate one of the received audio signals (or combination of signals) for transmission to the hearing device. In an embodiment, the auxiliary device is or comprises a remote control for controlling functionality and operation of the hearing device(s). In an embodiment, the function of a remote control is implemented in a SmartPhone, the SmartPhone possibly running an APP allowing to control the functionality of the audio processing device via the SmartPhone (the hearing device(s) comprising an appropriate wireless interface to the SmartPhone, e.g. based on Bluetooth or some other standardized or proprietary scheme). In an embodiment, the auxiliary device is or comprises a smartphone or equivalent communication device allowing to be connected to the hearing assistance system via a communication link and having appropriate processing power and/or being capable of functioning as a user interface to the hearing assistance system.

A Hearing Device:

In an embodiment, the hearing device is adapted to provide a frequency dependent gain and/or a level dependent compression and/or a transposition (with or without frequency compression) of one or frequency ranges to one or more other frequency ranges, e.g. to compensate for a hearing impairment of a user. In an embodiment, the hearing device comprises a signal processing unit for enhancing the input signals and providing a processed output signal.

In an embodiment, the hearing device comprises an output unit for providing a stimulus perceived by the user as an acoustic signal based on a processed electric signal. In an embodiment, the output unit comprises a number of electrodes of a cochlear implant or a vibrator of a bone conducting hearing device. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing device). In an embodiment, the hearing device comprises a speakerphone (comprising a number of input transducers and a number of output transducers, e.g. for use in an audio conference situation).

In an embodiment, the hearing device comprises an input unit for providing an electric input sound signal representing sound. In an embodiment, the input unit comprises an input transducer, e.g. a microphone, for converting an input sound to an electric input sound signal. In an embodiment, the input unit comprises a wireless receiver for receiving a wireless signal comprising sound and for providing an electric input sound signal representing said sound. In an embodiment, the hearing device comprises a directional microphone system adapted to spatially filter sounds from the environment, and thereby enhance a target acoustic source relative to a multitude of other acoustic sources in the local environment of the user wearing the hearing device. In an embodiment, the directional system is adapted to detect (such as adaptively detect) from which direction a particular part of the microphone signal originates. This can be achieved in various different ways as e.g. described in the prior art.

In an embodiment, the hearing device comprises an antenna and transceiver circuitry for wirelessly receiving a direct electric input signal from another device, e.g. a communication device or another hearing device. In an embodiment, the hearing device comprises a (possibly standardized) electric interface (e.g. in the form of a connector) for receiving a wired direct electric input signal from another device, e.g. a communication device or another hearing device. In an embodiment, the communication between the hearing device and the other device is in the base band (audio frequency range, e.g. between 0 and 20 kHz). Preferably, communication between the hearing device and the other device is based on some sort of modulation at frequencies above 100 kHz. Preferably, frequencies used to establish a communication link between the hearing device and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology).

In an embodiment, the hearing device is portable device, e.g. a device comprising a local energy source, e.g. a battery, e.g. a rechargeable battery.

In an embodiment, the hearing device comprises a forward or signal path between an input transducer (microphone system and/or direct electric input (e.g. a wireless receiver)) and an output transducer. In an embodiment, the signal processing unit is located in the forward path. In an embodiment, the signal processing unit is adapted to provide a frequency dependent gain (amplification or attenuation) according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or $x[n]$) at discrete points in time $t_n$ (or n), each audio sample representing the value of the acoustic signal at $t_n$ by a predefined number $N_s$ of bits, $N_s$ being e.g. in the range from 1 to 48 bits, e.g. 24 bits. A digital sample x has a length in time of $1/f_s$, e.g. 50 µs, for $f_s=20$ kHz. In an embodiment, a number of audio samples are arranged in a time frame. In an embodiment, a time frame comprises 64 or 128 audio data samples. Other frame lengths may be used depending on the practical application.

In an embodiment, the hearing devices comprise an analogue-to-digital (AD) converter to digitize an analogue input with a predefined sampling rate, e.g. 20 kHz. In an embodiment, the hearing devices comprise a digital-to-analogue (DA) converter to convert a digital signal to an analogue output signal, e.g. for being presented to a user via an output transducer.

In an embodiment, the hearing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the frequency domain. In an embodiment, the frequency range considered by the hearing device from a minimum frequency $f_{min}$ to a maximum frequency $f_{max}$ comprises a part of the typical human audible frequency range from 20 Hz to 20 kHz, e.g. a part of the range from 20 Hz to 12 kHz. In an embodiment, a signal of the forward and/or analysis path of the hearing device is split into a number NI of frequency bands, where NI is e.g. larger than 5, such as larger than 10, such as larger than 50, such as larger than 100, such as larger than 500, at least some of which are processed individually. In an embodiment, the hearing device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing device comprises a number of detectors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing assistance device, a remote control, and audio delivery device, a telephone (e.g. a Smartphone), an external sensor, etc.

In an embodiment, one or more of the number of detectors operate(s) on the full band signal (time domain). In an embodiment, one or more of the number of detectors operate(s) on band split signals ((time-) frequency domain).

In an embodiment, the number of detectors comprises a level detector for estimating a current level of a signal of the forward path. In an embodiment, the predefined criterion comprises whether the current level of a signal of the forward path is above or below a given (L–)threshold value.

In a particular embodiment, the hearing device comprises a voice detector (VD) for determining whether or not (or with what probability) an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the hearing device comprises an own voice detector for detecting whether a given input sound (e.g. a voice) originates from the voice of the user of the system. In an embodiment, the microphone system of the hearing device is adapted to be able to differentiate between a user's own voice and another person's voice and possibly from NON-voice sounds.

In an embodiment, the hearing assistance device comprises a classification unit configured to classify the current situation based on input signals from (at least some of) the detectors, and possibly other inputs as well. In the present context 'a current situation' is taken to be defined by one or more of a) the physical environment (e.g. including the current electromagnetic environment, e.g. the occurrence of electromagnetic signals (e.g. comprising audio and/or control signals) intended or not intended for reception by the hearing device, or other properties of the current environment than acoustic;

b) the current acoustic situation (input level, feedback, etc.), and c) the current mode or state of the user (movement, temperature, etc.);

d) the current mode or state of the hearing assistance device (program selected, time elapsed since last user interaction, etc.) and/or of another device in communication with the hearing device.

In an embodiment, the hearing device further comprises other relevant functionality for the application in question, e.g. feedback suppression, compression, noise reduction, etc.

Use:

In an aspect, use of a hearing device as described above, in the 'detailed description of embodiments' and in the claims, is moreover provided. In an embodiment, use is provided in a system comprising audio distribution. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A Method:

In a third aspect, a method of automatically selecting an audio source intended to be listened to by a wearer of a hearing device in a multi-audio source environment is furthermore provided by the present application. The method comprises providing electric input sound signals $u_i$, each representing sound signals $U_i$ from a multitude $n_u$ of sound sources $S_i$ (i=1, . . . , $n_u$), recording activity of the auditory system of the user's brain and providing a multitude $n_y$ of EEG signals $y_j$ (j=1, . . . , $n_y$), and providing a source selection signal $\hat{S}_x$ indicative of the sound source $S_x$ that the user currently pays attention to in dependence of said electric input sound signals $u_i$ and said EEG signals $y_j$, analyzing said electric input sound signals $u_i$ i=1, . . . , $n_u$, and said multitude of EEG signals $y_j$, j=1, . . . , $n_y$, using a selective algorithm that determines a sparse model to select the most relevant EEG electrodes and time intervals based on minimizing a cost function measuring the correlation between the sound source and the EEG signals, and determining the source selection signal $\hat{S}_x$ indicative of the sound source $S_x$ that the user currently pays attention to based on the cost function obtained for said multitude of sound sources.

In a fourth aspect, a method of automatically selecting an audio source intended to be listened to by a wearer of a hearing device in a multi-audio source environment is furthermore provided by the present application. The method comprises providing electric input sound signals $u_i$, each representing sound signals $U_i$ from a multitude $n_u$ of sound sources $S_i$ (i=1, . . . , $n_u$), recording activity of the auditory system of the user's brain and providing a multitude $n_y$ of EEG signals $y_j$ (j=1, . . . , $n_y$), and providing a source selection signal $\hat{S}_x$ indicative of the sound source $S_x$ that the user currently pays attention to in dependence of said electric input sound signals $u_i$ and said EEG signals $y_j$, including analyzing said electric input sound signals $u_i$ $i=1, \ldots, n_u$, and said multitude of EEG signals $y_j$, $j=1, \ldots, n_y$, to determine a dynamic finite impulse response (FIR) filter from each sound source to each EEG channel, and to determine the source selection signal $\hat{S}_x$ indicative of the sound source $S_x$ that the user currently pays attention to based on cost functions obtained for said multitude of sound sources.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

In an embodiment, the method comprises using a stimuli reconstruction (SR) method for estimating the FIR inverse model from EEG signal to sound source.

In an embodiment, the method comprises using a sparse model for modeling the finite impulse response (FIR) filter from each sound source to each EEG channel.

In an embodiment, the method comprises using the alternating direction method of multipliers (ADMM) methodology to reformulate the optimization problem into another one with different B vectors in the cost function.

In an embodiment, the method comprises analyzing said electric input sound signals $u_i$ $i=1, \ldots, n_u$, and said multitude of EEG signals $y_j$, $j=1, \ldots, n_y$, wherein said selective algorithm is based on providing a full FIR single input multiple output (SIMO) model for each electric input sound signal $u_i$, based on said electric input sound signals $u_i$, and said EEG signals $y_j$, and using an alternating direction of multipliers method (ADMM) to provide sparse models from said full FIR single input multiple output (SIMO) models for use in identifying the model that best describes the corresponding electric input sound signal and EEG signal data, and determining the sound source $S_x$ that the user currently pays attention to by comparing cost functions of each model.

In an embodiment, the method comprises the following steps aimed at understanding how the human auditory system reacts when exposed to different sound sources and attending to one of these sources, providing a standard causal multi input multiple output (MIMO) finite impulse response (FIR) model of order k from sound to EEG for each electric input sound signal $u_i$, to each EEG signal $y_j$, and using an alternating direction of multipliers method (ADMM) to provide a sparse model that automatically selects the EEG channels and parameters of the FIR model, including time delay and model order k, of the highest relevance.

In an embodiment, the method comprises providing that an order k of the FIR MIMO model is selected with a view to the time span wherein a speech signal has an effect on simultaneously recorded EEG signals. In an embodiment, the order k of the FIR MIMO model is selected with a view to the time span (also referred to as time lags) wherein a (given) speech signal has an (substantial) effect on the EEG signals (neural response to the speech signal). In an embodiment, the order of k is chosen to provide that time lags covering a range from 0.5 s to 5 s, such as 0.5 to 2 s, are considered by the model. In an embodiment, the order k of the FIR MIMO model is selected in the range from 30 to 600, such as in the range from 50 to 100.

In an embodiment, a feed filter B is obtained with an ADMM to linear support vector machine (SVM) algorithm ($Y=U_i*B_i$, $U_i$=sound, Y=EEG).

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

An APP:

In a further aspect, a non-transitory application, termed an APP, is furthermore provided by the present disclosure. The APP comprises executable instructions configured to be executed on an auxiliary device to implement a user interface for a hearing device or a hearing assistance system described above in the 'detailed description of embodiments', and in the claims. In an embodiment, the APP is configured to run on cellular phone, e.g. a smartphone, or on another portable device allowing communication with said hearing device or said hearing system.

In an embodiment, the APP is configured to allow a user to initiate a procedure for estimating a current sound source of the user's attention according to the present disclosure (e.g. according to the method described above, in the detailed description or in the claims). In an embodiment, the APP is configured to display currently present sound sources relative to the user. In an embodiment, the APP is configured to indicate a relative strength of the currently active sound sources. In an embodiment, the APP is configured to allow a user to select a sound source of current interest to the user among the currently active sound sources. In an embodiment, the APP is configured to allow a user to select relative weights of the currently active sound sources.

Definitions

In the present context, a 'hearing device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing device may comprise a single unit or several units communicating electronically with each other.

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit for processing the input audio signal and an output means for providing an audible signal to the user in dependence on the processed audio signal. In some hearing devices, an amplifier may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output means may comprise an output transducer, such as e.g. a loudspeaker for providing an air-borne acoustic signal or a vibrator for providing a structure-borne or liquid-borne acoustic signal. In some hearing devices, the output means may comprise one or more output electrodes for providing electric signals.

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A 'hearing assistance system' may refer to a system comprising one or two hearing devices, and a 'binaural hearing assistance system' may refer to a system comprising two hearing devices and being adapted to cooperatively provide audible signals to both of the user's ears. Hearing assistance systems or binaural hearing assistance systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. SmartPhones), public-address systems, car audio systems or music players. Hearing devices, hearing assistance systems or binaural hearing assistance systems may e.g. be used for compensating for a hearing-impaired person's loss of hearing capability, augmenting or protecting a normal-hearing person's hearing capability and/or conveying electronic audio signals to a person.

Embodiments of the disclosure may e.g. be useful in applications such as hearing aids, headsets, ear phones, active ear protection systems, handsfree telephone systems, mobile telephones, teleconferencing systems, public address systems, karaoke systems, classroom amplification systems, etc.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Figure 1A:
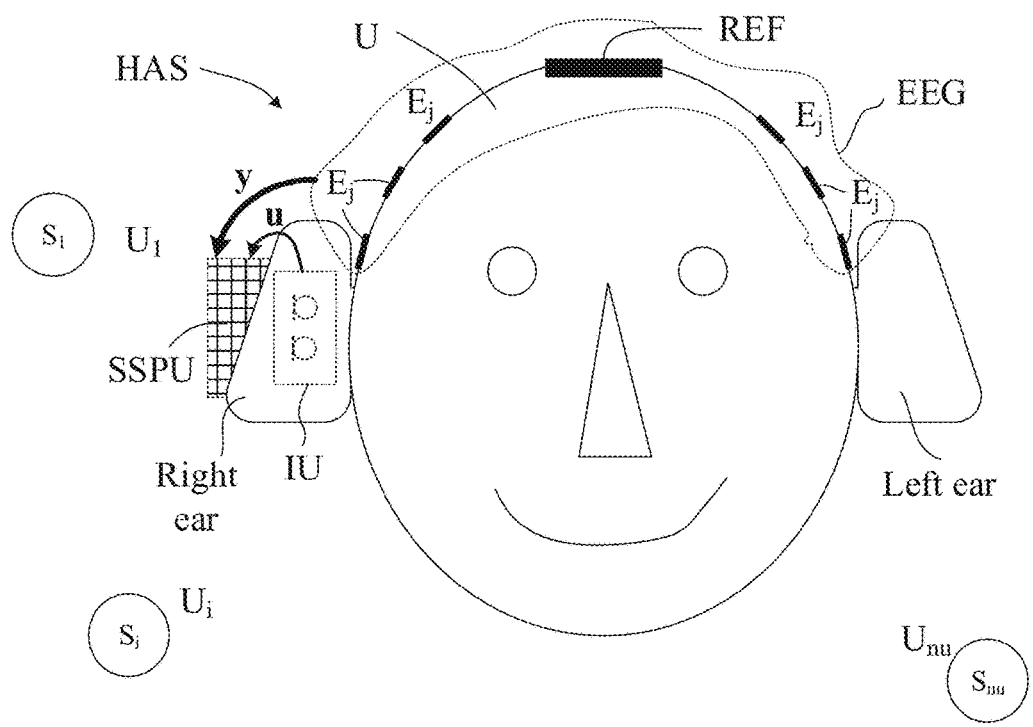
FIG. 1A shows a multi-sound source acoustic environment with a user wearing a first embodiment of a hearing assistance system comprising an EEG system according to the present disclosure.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing assistance systems, including devices, e.g. hearing aids. The disclosure deals in particular with the problem of speech representation in the human brain and the so-called cocktail-party problem, that is, a separation of a single sound source of the listener's interest from the multitude of sound sources in a noisy and crowded background. The routine with which the human brain solves the cocktail-party problem hides the intrinsic problem complexity: (1) different competing sound sources emit different sound signals concurrently, (2) these signals are then mixed, (3) the sum of these signals enters the ear(s) (4) which is later on decoupled, (5) a sound signal of interest is selected and (6) the other sound signals are tuned out within the auditory system. Although the cocktail party problem has been around for decades, cocktail party problem solving seems to be an underdeveloped field. We still have very little knowledge about how our brain solves it and many questions still remain unanswered.

A number of patent applications and patents by the present inventors deal with measuring brain wave signals (e.g. EEG signals) using one or more electrodes located on or in connection with a hearing aid, cf. e.g. [16], [17], [18], [23].

Previous studies described several conceptually different approaches to understand how the brain solves the cocktail party problem. The bottom line of all these approaches is the realization that the different sound sources excite different neural responses and that the brain activity follows the sound amplitude envelope. Most of the studies adhere to stimulus reconstruction (SR) approach, an inverse model from neural response, that is, brain signals y(t), to speech u(t). The literature on stimulus reconstruction is almost as considerable as that on selective attention.

The decision on how the SR is to be performed is quite subjective and is usually the result of the compromise between different aspects, which include flexibility, parsimony, usage intention, recording modality type, computation cost, etc. In general, SR boils down to performing linear regression (LR). Recently, more a sophisticated method based on deep neural networks (DNNs) was proposed in lieu of LR. DNN proved to be more helpful in understanding the speech influence on the brain activity, its representation and reconstruction, but the pay-off is the higher complexity and thus higher computational burden.

It should be noted that appealing results were obtained for SR applied to electrocorticographic (ECoG) data and magnetoencephalographic (MEG) data, but the particular problem with ECoG and MEG data which makes them less attractive are invasiveness of ECoG to the brain tissues and lack of portability of MEG instruments. In lieu of ECoG and MEG instruments, EEG instruments are noninvasive, portable and readily available what makes them more suitable and attractive (e.g. for hearing devices, such as hearing aids). Moreover, it was shown that attention can be decoded from EEG data with SR [21]. Whenever we need to compare the results for our model with models found in literature, we shall adhere to the article of O'Sullivan et. al. [21] since it is the representative article between the multitude of researches on the SR, selective attention and solving the cocktail-party problem in general.

To conclude, there are three key reasons why SR is attractive:

It can be used to find time scales with stimuli information in neural responses.
It can be used in neural signal processing.
It can be used in solving the cocktail party problem to some extent, that is, in gaining deeper understanding of the speech representation and reconstruction and selecting the attended speech stream in a multi-talker background.

On the negative side, SR model corresponds to an anti-causal model, and the downsides are the lack of understanding of dynamical effects and difficulty in real-time implementation, so in practice there might be no benefit from SR. It must be stressed that in off-line application, stimulus reconstruction (SR) can still be used for data analysis and understanding auditory subcomponent of connectome (a 'connectome' being a network map illustrating interactions in the nervous system).

A particular interest lies in obtaining a reliable model to deeper understand the attention in hearing, in particular, how the sound is represented in the brain and how to correctly identify the speech stream that the listener currently attends to. This identification should preferably be performed in real time. In other words, the identification of the sound source, referred to as $S_i$ (or just i), and the corresponding sound source signal $u_i$, which is attended to by the listener at time t, cannot be obtained at a later time $t_1$, where $t_1 > t$. This is, on the other hand, the case when using SR methods.

The present disclosure proposes to overcome the above pitfalls by formulating a causal, multivariate finite impulse response (FIR) model from speech to EEG, and to subsequently use an alternating direction of multipliers method (ADMM) to get a sparse model that automatically selects the EEG channels and FIR parameters (including time delay and model order) of the highest relevance. Besides a sparse model, it also gives physical insights. If the model is well-conditioned, it is likely that it will also indicate the attended sound source. An advantage of the approach (in addition to its real time realization) is that a software implementation can be made relatively simple and efficient.

Since the present disclosure is focused on hearing devices, e.g. hearing aids, requiring on-line (real time) applications, we consider only brain signal data recorded with EEG instruments, for the reasons mentioned above.

The present disclosure provides a hearing assistance system and a method for identifying a specific sound source in multi-sound source (e.g. multi-talker) background in real-time using un-averaged single-trial EEG.

The model suggested in the present disclosure for the identification of the speech stream currently attended to by a wearer of the hearing assistance system will be referred to as the CLassification of Attended speech STream In Cocktail-party problem (CLASTIC) model.

The cocktail party problem arises when a number of different (constant or time-variant) competing sources $S_i$, i=1, 2, . . . , $n_u$, emit sound signals $U_i$ (represented by electric input sound signals $u_i$) simultaneously and a listener receives the sum ($u_{total}$) of these signals, i.e., $$u_{total} = \sum_{i=1}^{n_u} u_i(t) \quad (1)$$

Under the assumption that the listener is attempting to focus on only one sound source (e.g. a speech stream) at a time, the technical challenge is to identify which of the speech signals $u_i(t)$ is the subject of focus by the listener (user of the hearing assistance system). This is proposed to be done based on external sensor measurements, here, EEG signals, $y_j(t)$, with j=1, 2, . . . , $n_y$.

Figure 1B:
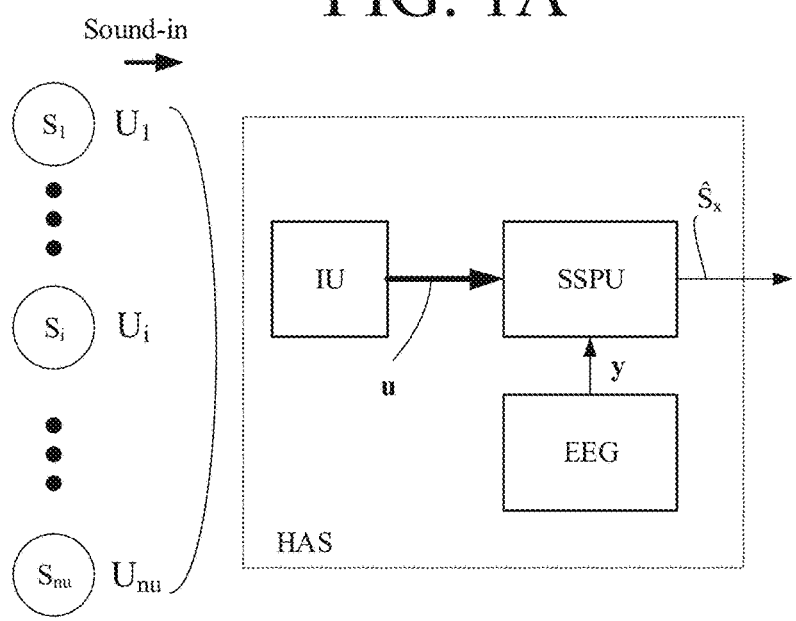
FIG. 1B shows a simplified block diagram of the first embodiment of a hearing assistance system shown in FIG. 1A.
Figure 1C:
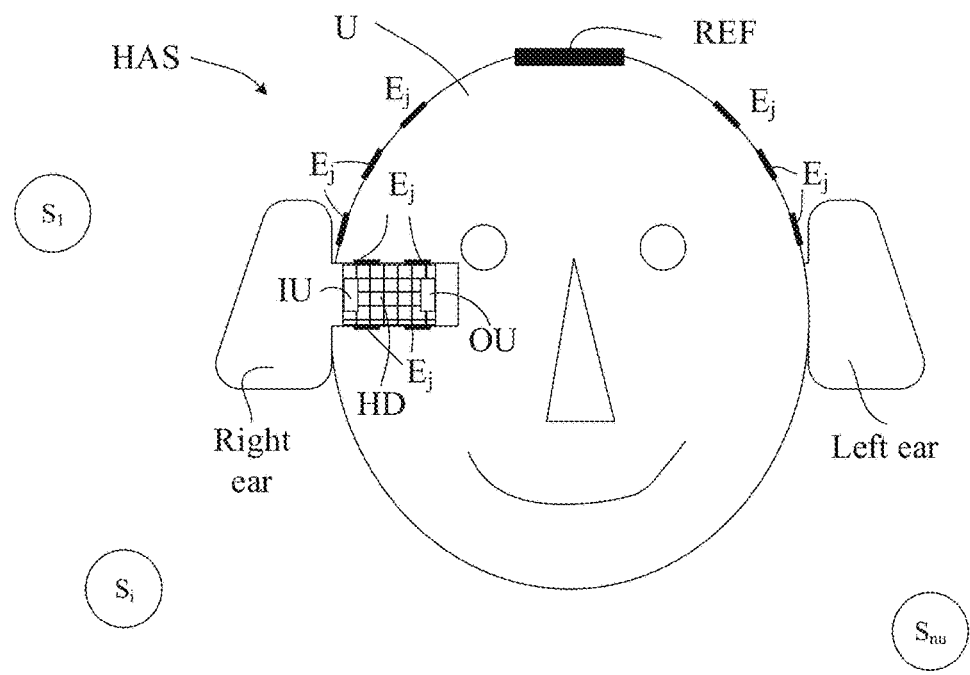
FIG. 1C shows a multi-sound source acoustic environment with a user wearing a second embodiment of a hearing assistance system comprising an EEG system according to the present disclosure.
Figure 1D:
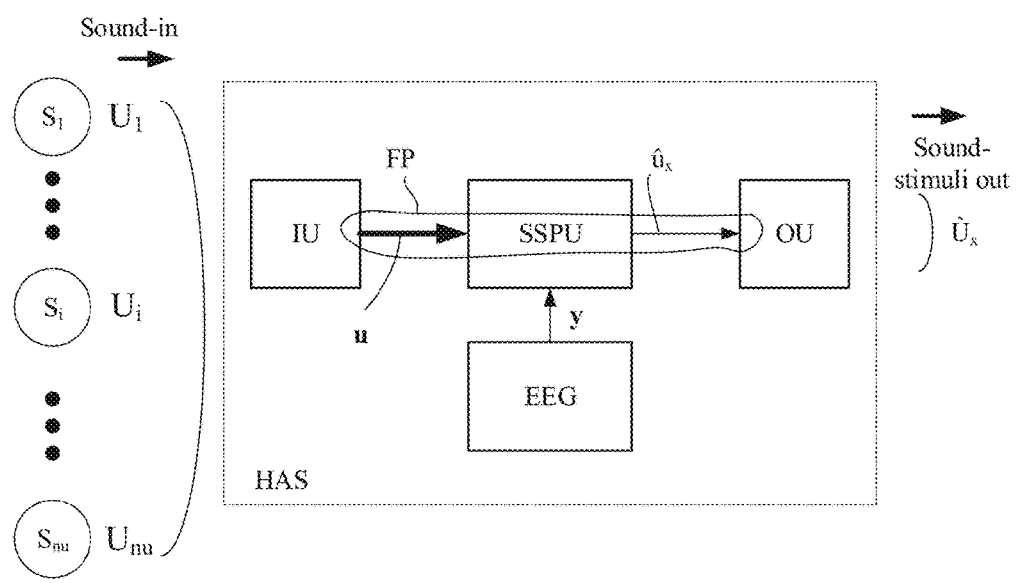
FIG. 1D shows a simplified block diagram of the second embodiment of a hearing assistance system shown in FIG. 1C.
Figure 1E:
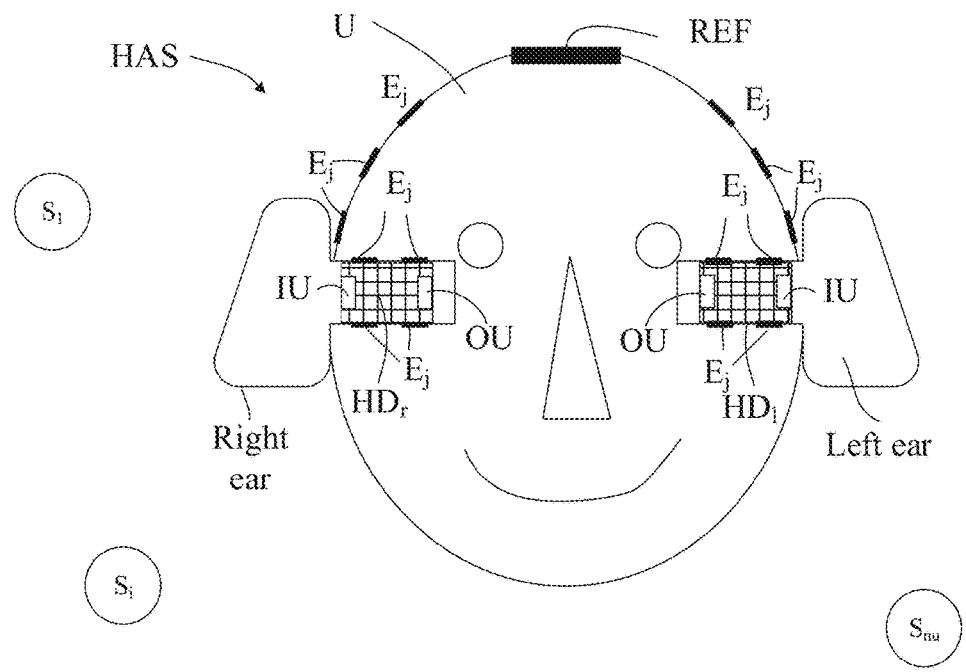
FIG. 1E shows a multi-sound source acoustic environment with a user wearing a third embodiment of a hearing assistance system comprising an EEG system according to the present disclosure.
Figure 1F:
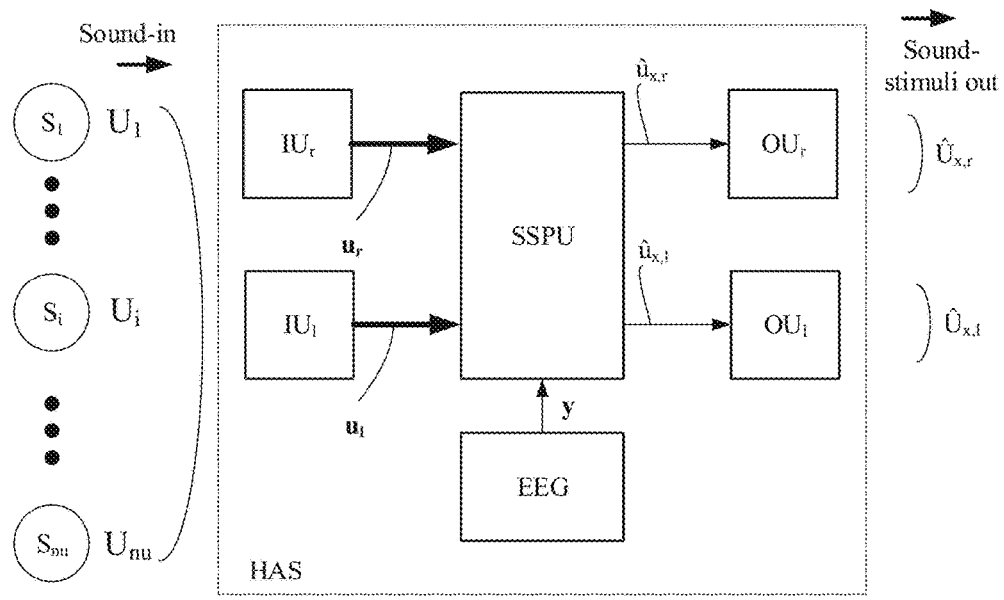
FIG. 1F shows a simplified block diagram of the third embodiment of a hearing assistance system shown in FIG. 1E.
Figure 1G:
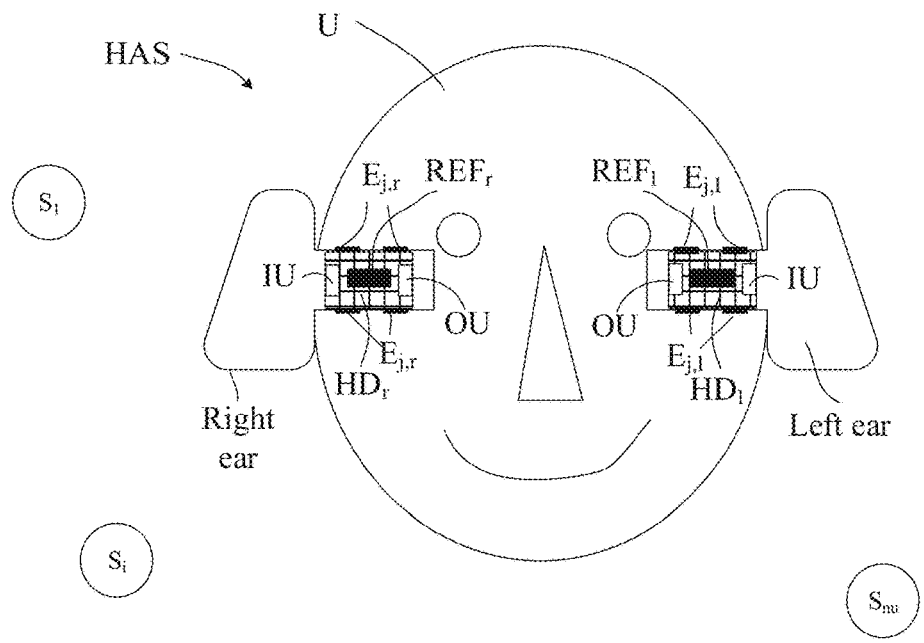
FIG. 1G shows a multi-sound source acoustic environment with a user wearing a fourth embodiment of a hearing assistance system comprising an EEG system according to the present disclosure.

FIG. 1A-FIG. 1J illustrate a multi-sound source acoustic environment ($S_i$, i=1, . . . , $n_u$) with a user (U) wearing first to fifth embodiments of a hearing assistance system (HAS) comprising an EEG system (EEG) according to the present disclosure (cf. sound sources $S_1$, . . . , $S_i$, . . . $S_{nu}$ around the user U in FIGS. 1A, 1C, 1E, 1G, 1I). The hearing assistance system (HAS) comprises an input unit (IU) for providing electric input sound signals $u_i$, each representing sound signals $U_i$ from the multitude $n_u$ of sound sources $S_i$ (i= 1, . . . , $n_u$) (cf. bold arrow denoted 'Sound in' in FIGS. 1B, 1D, 1F, 1H, 1J). The input unit may comprise a sound source separation algorithm for providing said electric input sound signals $u_i$ from a number of signals (e.g. microphone signals) comprising a mixture of said sound signals $U_i$. The hearing assistance system (HAS) further comprises an electroencephalography (EEG) system for recording activity of the auditory system of the user's brain and providing a multitude $n_y$ of EEG signals $y_j$ (j=1, . . . , $n_y$). The hearing assistance system (HAS) further comprises a source selection processing unit (SSPU) coupled to said input unit (IU) and to said EEG-system (EEG) and receiving said electric input sound signals $u_i$ (i=1, . . . , $n_u$) and said EEG signals $y_j$ (j=1, . . . , $n_y$). The hearing assistance system (HAS) is configured to provide a source selection signal $\hat{S}_x$ indicative of the sound source $S_x$ that the user currently pays attention to in dependence of the electric input sound signals $u_i$ and the EEG signals $y_j$. The EEG-system (EEG) comprises EEG sensors with electrodes $E_j$, and a reference electrode REF. The hearing assistance system may comprise an output unit (OU) for providing output stimuli perceivable by the user as sound, based on an estimate $\hat{u}_x$ of the sound signal $U_x$ (or mixture of sound signals) from the sound source $S_x$ that the user currently pays (or is estimated to pay) attention to. The hearing assistance system may comprise one or more (e.g. two) hearing devices, e.g. hearing aids (cf. e.g. FIGS. 1C, 1E, 1G). The hearing device may comprise the or an output unit (OU) for providing output stimuli perceivable by the user as sound based on the source selection signal $\hat{S}_x$ indicative of the sound source $S_x$ that the user currently pays attention to. The EEG-system may be fully external to the hearing device(s) (as e.g. shown in FIGS. 1A and 1I), or fully integrated in the hearing device (see e.g. FIG. 1G), or be partially integrated with and partially external to the hearing device (as in FIG. 1C and FIG. 1E). The hearing device(s) of FIGS. 1C, 1E, 1G may comprise a BTE-part adapted for being mounted at or behind an ear (BTE, e.g. behind pinna) of the user. The hearing device may alternatively or additionally comprise an ITE-part adapted for being mounted at or in an ear canal of the user. The EEG-electrodes may e.g. be located on a BTE-part and/or on an ITE-part. In the examples of FIGS. 1C, 1E, and 1G, four EEG-electrodes are (schematically) shown on an ITE-part of the hearing device, but other numbers and locations can be envisioned, e.g. one or more, such as two or more). In the embodiment of FIG. 1G, four EEG-electrodes ($E_{j,r}$, $E_{j,l}$) and one reference electrode ($REF_r$, $REF_l$) are shown on each hearing device ($HD_r$, $HD_l$, here located on ITE-parts of the hearing devices. In the embodiment of FIGS. 1A, 1C, 1E, 1J, the EEG system is shown to comprise a number of EEG-electrodes $E_j$ located on the scalp of the user (U). In these embodiments, six EEG-electrodes $E_j$ and a reference electrode REF are (schematically) shown. Other numbers may of course be used according to the application. If a part of the EEG-system comprising electrodes on the scalp of the user has to be dispensed with, so that all EEG-electrodes are to be located on one or two hearing device(s), a relatively small number of electrodes will typically be used (e.g. limited by the surface area of the housing of the hearing device(s)). In case an 'external' (i.e. not limited to the hearing device(s)) EEG-part can be used, a larger number of EEG-electrodes, e.g. more than 20, such as more than 50, such as more than 100 electrodes can be used. In the embodiments, of FIGS. 1A, 1C, 1E, 1J, a reference electrode REF is located at the top of the scalp of the user (in a symmetry plane of the user's head). Alternatively, a reference electrode may be located elsewhere, e.g. behind an ear (at a mastoid part of the temporal bone), or implanted in the head. In an embodiment, where all electrodes are integrated in the hearing device, or in a pair of hearing devices (cf. e.g. FIG. 1G), the reference electrode can be located in the same hearing device as the EEG-electrodes. Preferably, the reference electrode is located a distance apart from the EEG-electrodes, e.g. in a contra-laterally located hearing device (cf. e.g. FIG. 1G). In such case the reference potential of the opposite hearing device can be transferred to the hearing device comprising the EEG-electrodes by a galvanic (e.g. wired) connection or by transfer via a wireless communication link, e.g. via the body of the user (body network, cf. e.g. EP2997893A1).

A number of methods are available in the art to provide (real-time) separation of sound sources from one or more signals comprising a mixture of the sound sources. These methods include blind source separation, means of e.g. blind source separation, cf. e.g. [Bell and Sejnowski, 1995], [Jourjine et al., 2000], [Roweis, 2001], [Pedersen et al., 2008], microphone array techniques, cf. e.g. chapter 7 in [Schaub, 2008], or combinations hereof, cf. e.g. [Pedersen et al., 2006], [Boldt et al., 2008]. Other methods include Nonnegative Matrix Factorization (NMF), Probabilistic Latent Component Analysis (PLCA). A real time separation method based on modelling the contents of a buffer comprising a time segment of the mixed signal as an additive sum of components, which are stored in pre-computed dictionaries is e.g. disclosed in US2016099008A1.

Figure 1H:
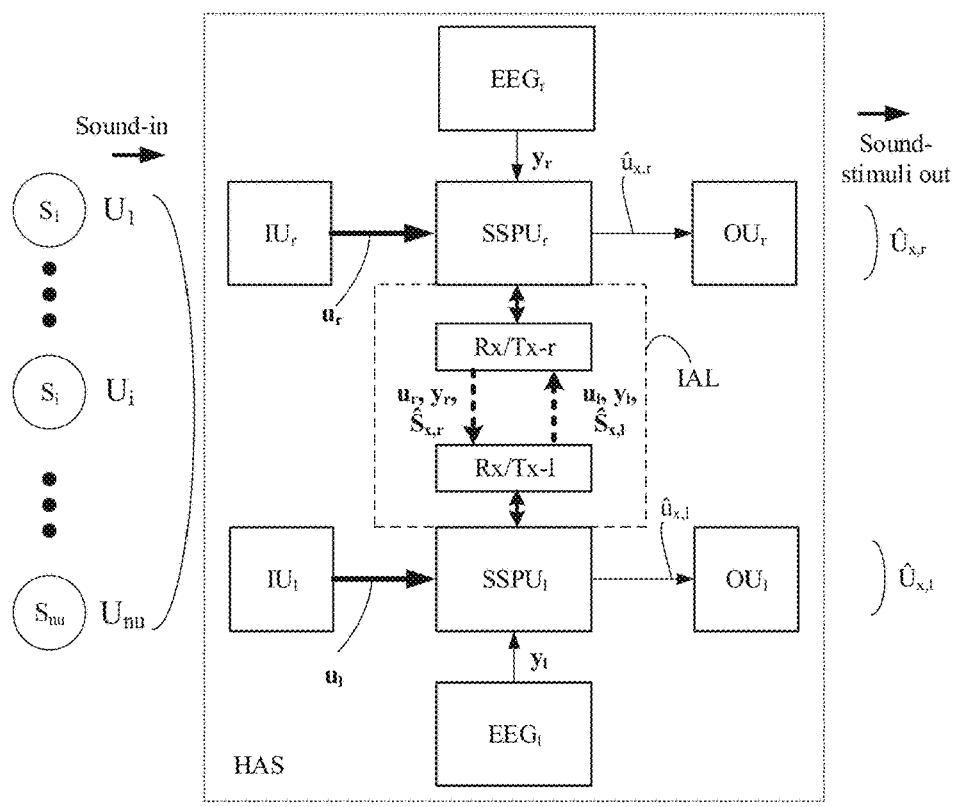
FIG. 1H shows a simplified block diagram of the fourth embodiment of a hearing assistance system shown in FIG. 1G.
Figure 1I:
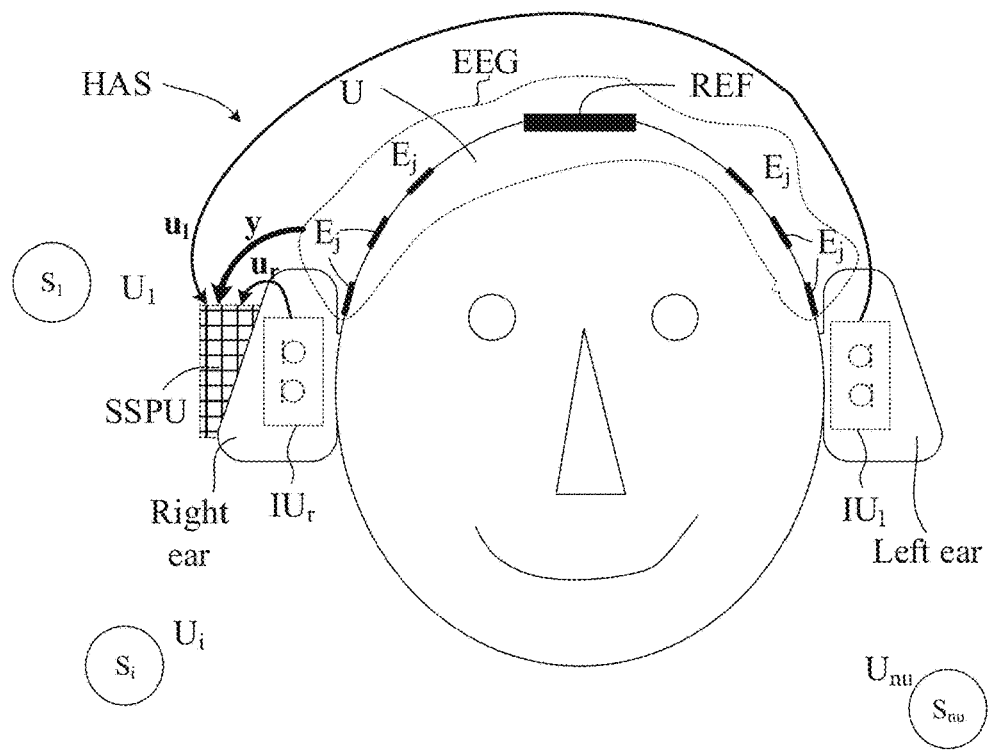
FIG. 1I shows a multi-sound source acoustic environment with a user wearing a fifth embodiment of a hearing assistance system comprising an EEG system according to the present disclosure.

FIGS. 1A and 1I show (first and fifth) embodiments of a hearing assistance system (HAS) comprising one or more input units (IU; $IU_r$, $IU_l$)) (each being) located at an ear of a user, an EEG-system (EEG) and a sound source selection processing unit (SSPU) in operational communication with each other. An input unit (IU) may e.g. comprise one, or two, or more microphones located at an ear of the user, e.g. one located at an ear canal (e.g. at the entrance to the ear canal) and/or one or more located at or behind pinna or elsewhere at or around the ear (e.g. fully or partly implanted in the head at the ear of the user). The EEG-system (EEG) comprising EEG sensors/electrodes $E_j$ (j=1, . . . , $n_y$) and reference electrode REF provides EEG signals $y_j$ (j=1, . . . , $n_y$) to the source selection processing unit (SSPU). The EEG-signals $y_j$ each represent a potential picked up by electrode j ($E_j$) relative to reference potential picked up by the reference electrode (REF). In the embodiments of FIGS. 1A and 1I the EEG sensors/electrodes and the reference electrode are located on the scalp of the user's head. One or more (such as all) of the electrodes may be implanted in the head of the user, e.g. in connection with a cochlear implant type of hearing aid or a bone conduction type hearing aid. In an embodiment, the potentials $P_j$ are individually guided to a comparison unit (e.g. a comparator or an analogue to digital (AD) converter) where it is compared with the reference potential $P_{REF}$ to provide respective EEG-signals $y_j$ (e.g. as $P_j - P_{REF}$, j=1, . . . $n_y$).

FIG. 1A shows a first embodiment of a hearing assistance system (HAS) comprising a single input unit (IU) located at the right ear (Right ear) of the user (U). FIG. 1B shows a simplified block diagram of the first embodiment of a hearing assistance system shown in FIG. 1A. The input unit (IU) provides (separated) electric input sound signals $u_i$ (i=1, . . . , $n_u$), to the source selection processing unit (SSPU) (cf. vector u in FIGS. 1A and 1B). The EEG-system provides EEG signals $y_j$ (j=1, . . . , $n_y$) to the source selection processing unit (SSPU) (cf. vector y in FIGS. 1A and 1B). The source selection processing unit (SSPU) provides a source selection signal $\hat{S}_x$ indicative of the sound source $S_x$ that the user currently pays attention to based on the electric input sound signals $u_i$, and on the EEG signals $y_j$ (cf. signal $\hat{S}_x$ in FIG. 1B) as described below.

Figure 1J:
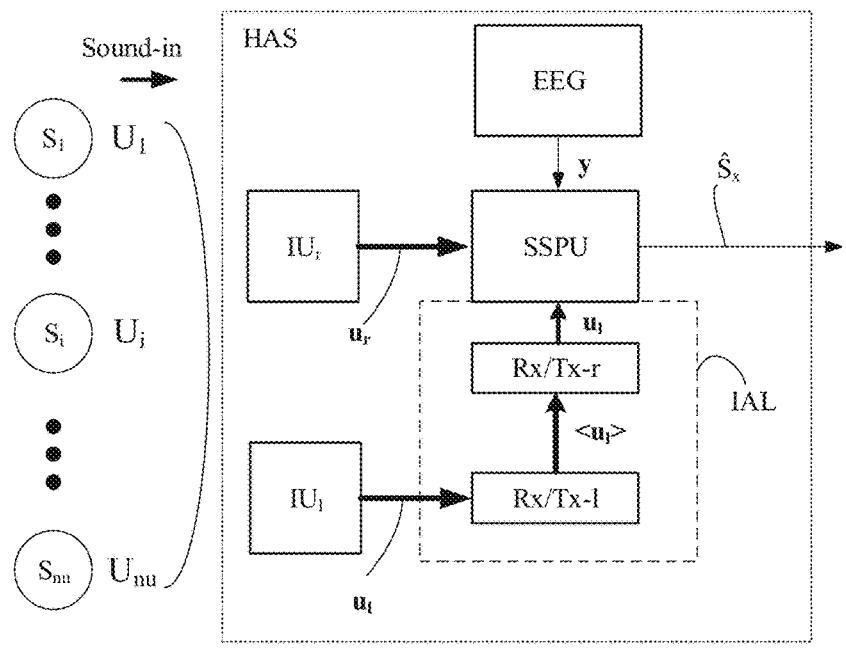
FIG. 1J shows a simplified block diagram of the fifth embodiment of a hearing assistance system shown in FIG. 1I.

FIG. 1I shows a fifth embodiment of a hearing assistance system (HAS) comprising two input units ($IU_r$, $IU_l$) located at the right ear (Right ear) and left ear (Left ear), respectively, of the user (U). The fifth embodiment is equal to the first embodiment (of FIGS. 1A, 1B) apart from the fifth embodiment comprising a bilateral or binaural setup where separate input units are located at the right and left ears of the user thereby providing electric input sound signals $u_{i,r}$ and $u_{i,l}$ from the right and left input units ($IU_r$ and $IU_l$), respectively. FIG. 1J shows a simplified block diagram of the fifth embodiment of a hearing assistance system shown in FIG. 1I. The electric input sound signals $u_{i,r}$ and $u_{i,l}$ (together providing (separated) electric input sound signals $u_i$ (i=1, . . . , $n_u$)) are fed to the source selection processing unit (SSPU) (cf. vector $u_r$ and $u_l$ in FIGS. 1I and 1J) together with EEG signals $y_j$ (j=1, . . . , $n_y$) (cf. vector y in FIGS. 1I and 1J). The source selection processing unit (SSPU) may be located at one of the ears of the user (as shown in FIGS. 1A and 1I) or elsewhere, e.g. worn by or implanted in the body of the user. In the embodiment of FIG. 1J, the separated signals $u_l$ from the input unit $IU_l$ at the left ear are transmitted (e.g. wirelessly transmitted, e.g. via communication link IAL, e.g. implemented by respective transceiver units Rx/Tx-r and Rx/Tx-l, and signal $<u_l>$) to the source selection processing unit (SSPU). Other partitions may be implemented, e.g. to provide that the separated signals $u_r$ from the input unit $IU_r$ at the right ear are transmitted (e.g. wirelessly transmitted) to the source selection processing unit (SSPU) or that both of the separated signals $u_r$ and $u_l$ are transmitted to a source selection processing unit (SSPU), e.g. located in a separate (auxiliary) device, e.g. a remote control or a smartphone or other appropriate portable device. In an embodiment, the input signals before a source separation is performed are fed to a modified source selection processing unit (SSPU) where the source separation (and selection) is performed. The source selection processing unit (SSPU) provides a source selection signal $\hat{S}_x$ indicative of the sound source $S_x$ that the user currently pays attention to based on the electric input sound signals $u_{i,r}$, $u_{i,l}$ and on the EEG signals $y_j$ (cf. signal $\hat{S}_x$ in FIG. 1J) as described below.

The second embodiment of a hearing assistance system (HAS) shown in FIG. 1C comprises a hearing device (HD), e.g. a hearing aid, located at or in the right ear (Right ear) of the user (U) (or fully or partially implemented in the head of the user), whereas the left ear (Left ear) is not equipped with a hearing device. In other embodiments (as e.g. shown in FIGS. 1E, 1G) the hearing assistance system comprises two hearing devices located at respective left and right ears of the user. The hearing device (HD) comprises the input unit (IU) for providing electric input sound signals $u_i$ (u) and an output unit (OU) for providing output stimuli perceivable by the user as sound, based on an estimate $\hat{u}_x$ of the sound signal $U_x$ (from the sound source(s) $S_x$) that the user currently pays attention to (cf. bold arrow denoted 'Sound stimuli out, $\hat{U}_x$' in FIG. 1D). The source selection processing unit (SSPU) may be configured to provide the estimate $\hat{u}_x$ as a weighted combination of the electric input sound signals $u_i$ to the output unit(s) (OU). The source selection unit (SSPU) may be located in the hearing device (HD) or in another (e.g. auxiliary) device. In the embodiment of FIG. 1C, electrodes $E_j$ of the EEG system are located on the hearing device as well as on the scalp of the user (U). The EEG system provides EEG signals $y_j$ (y) to the source selection unit (SSPU) based on electric potentials $P_j$ relative to the reference potential $P_{REF}$. A forward path FP is indicated from the input unit (IU) to the output unit (OU) including electric input sound signals u, source selection unit (SSPU), and the estimate $\hat{u}_x$ of the sound signal $U_x$ that the user currently pays attention to. The forward path (FP) may be or form part of a forward path of the hearing device.

The hearing assistance systems shown in FIGS. 1E, 1F and in FIGS. 1G, 1H, respectively, comprises left and right hearing devices adapted to be worn at respective left and right ears of the user. The left and right hearing devices ($HD_l$, $HD_r$) each comprises an input unit, e.g. comprising a number of microphones, providing left and right electric input sound signals $u_l$, $u_r$, respectively. In the embodiments of FIGS. 1E, 1G, the EEG system is shown to comprise a number of EEG-electrodes $E_j$ located on the hearing device. Each of the left and right hearing devices further comprises an output unit ($OU_l$, $OU_r$) adapted to provide respective estimates $\hat{U}_{x,l}$ and $\hat{U}_{x,r}$ of the sound signal $U_x$ that the user currently pays attention to at the left and right ears of the user.

In the embodiment of FIG. 1E, additional EEG electrodes ($E_j$) and a reference electrode (REF) are located on the scalp of the user, whereas this is not the case in FIG. 1G.

As illustrated in FIG. 1F, the third embodiment (FIG. 1E) of the hearing assistance system comprises a common source selection unit (SSPU) that receives the electric input sound signals ($u_l$, $u_r$) from the input units ($IU_l$, $IU_r$) of the left and right hearing devices, and also receives all EEG signals y (from the electrodes $E_j$, located on the scalp as well as on the left and right hearing devices). The common source selection unit (SSPU) is configured to provide (electric signal) estimates $\hat{u}_{x,l}$ and $\hat{u}_{x,r}$ of the sound signal $U_x$ that the user currently pays attention to, which are fed to (or transmitted to) the respective output units ($OU_l$, $OU_r$) of the left and right hearing devices ($HD_l$, $HD_r$). Based thereon, the respective output units ($OU_l$, $OU_r$) generate corresponding output stimuli intended to be perceived by the user as sound.

In the embodiment of FIG. 1G, all EEG sensors/electrodes ($E_{j,l}$, $E_{j,r}$) are located on the left and right hearing devices ($HD_l$, $HD_r$) in corresponding EEG-units ($EEG_l$, $EEG_r$) providing respective EEG-signals ($y_l$, $y_r$), cf. FIG. 1H. The left and right hearing devices may operated as self-contained (independent) systems (e.g. in a first mode of operation, or if no link is available between the two hearing devices). In a (second) mode operation, the first and second hearing devices may exchange information via an interaural link (IAL), e.g. a wireless link. The information that may be exchanged, may include one or more of the respective source selection signal $\hat{S}_{x,l}$, $\hat{S}_{x,r}$ indicative of the sound source $S_x$ that the user currently pays attention to, the respective electric input sound signals $u_{i,r}$, $u_{i,l}$ ($u_l$, $u_r$) and the respective EEG signals $y_{j,l}$, $y_{j,r}$ ($y_l$, $y_r$, cf. FIG. 1H). The individual sound source selection units ($SSPU_l$, $SSPU_r$) provide respective (electric signal) estimates $\hat{u}_{x,l}$ and $\hat{u}_{x,r}$ of the sound signal $U_x$ that the user currently pays attention to, to the respective output units ($OU_l$, $OU_r$) of the left and right hearing devices ($HD_l$, $HD_r$). Based thereon, the respective output units ($OU_l$, $OU_r$) generate corresponding output stimuli $\hat{U}_{x,l}$, $\hat{U}_{x,r}$ intended to be perceived by the user as sound. In an embodiment, where an interaural link between the first and second hearing devices (e.g. via a third (auxiliary) device) is available, the mode of operation may be user configurable via a user interface (e.g. implemented in a remote control device, e.g. as an APP of a smartphone, cf. e.g. FIG. 6).

The multi-talker environment as illustrated in FIGS. 1A, 1B, 1C, 1D, 1E, 1F, 1G, 1H, 1I, and 1J includes in general $n_u$ different sound sources (speech streams) $u_i(t)$. In the example considered in the following, $n_u$=2. In general, a hearing assistance system according to the present disclosure comprises $n_y$ different EEG electrodes (and one or more REF electrodes) and provides $n_y$ corresponding EEG signals $y_j(t)$. In the example considered in the following, we have access to full-scalp EEG signals, with $n_y$=128. However, a smaller number of EEG sensors may be provided, e.g. fully or partially included in a hearing device (FIGS. 1C, 1D) or in a pair of hearing devices (FIGS. 1E, 1F, 1G, 1H) worn at or in the ears of the user (or fully or partially implanted in the head of the user).

Signal Modeling and Estimation:

A. A Forward Model:

We have $n_u$ sound sources $u_i(t)$, i=1, 2; ..., $n_u$ and $n_y$ EEG channels $y_j(t)$, j=1, 2, ..., $n_y$. Physically, the sound should causally affect the listening attention in the brain. We will constrain the dynamics to be linear finite impulse filter (FIR) $b_{ij}(t)$, so this causal relation is modeled as the convolution (moving average, weighted average)

$$y_j(t) = b_{ij} * u_i(t) + e_j(t) = \sum_{k=1} n_b b_{ij}(k) u_i(t-k) + e_j(t) \quad (2)$$

where $n_b$ is the model order (design parameter) of the FIR filter.

Having N samples of $u_i(t)$ and $y_j(t)$, the relation can be written in vector form as $$Y_j = \mathcal{H}(U_i) B_{ij} + E_j \quad (3)$$

where $Y_j = (y_j(1), \ldots, y_j(N))^T$ and similarly for U and E, while $B_{ij} = (b_{ij}(1), \ldots, b_{ij}(n_b))^T$ and $\mathcal{H}(U_i)$ is a Hankel matrix with elements $\mathcal{H}(U_i)^{mn} = u_i(m-n)$.

The least squares (LS) method estimates the FIR parameters by the minimizing argument (arg min) of the two norm of the estimation error $$\hat{B}_{ij} = \arg\min_B V_{ij}(B) \quad (4)$$

$$\hat{B}_{ij} = \arg\min_B \|Y_j - \mathcal{H}(U_i) B_{ij}\|_2^2 \quad (5)$$

$$\hat{B}_{ij} = \mathcal{H}(U_i)^\dagger Y_j \quad (6)$$

where $\mathcal{H}(U_i)^\dagger = (\mathcal{H}(U_i)^T \mathcal{H}(U_i))^T \mathcal{H}(U_i)^T$ denotes the pseudo inverse.

B. SR as a Reverse Model:

The SR method aims at estimating the FIR inverse model from EEG signal to sound source $$u_i(t) = a_{ij} * y_j(t) + v_i(t) = \sum_{k=1}^{n_a} a_{ij}(k) y_j(t+k) + v_i(t) \quad (7)$$

$$U_i = \mathcal{H}(Y_i) A_{ij} + V_i \quad (8)$$

The idea is of course not that the brain affects the sound, that is why time is reversed in the EEG signal so $y_j(t+k)$ is used rather than $y_j(t-k)$ in the convolution.

The notation here is dual to the forward model we propose. Though both methods look equivalent at first glance, there are several important differences:

- The forward model can be used to predict future values of the EEG signal, and is thus useful for classification of the attended source in a real-time application. The reverse model must be applied on batches, and is thus not as suitable for real-time classification.
- Even a short FIR filter in the forward model, may require a long FIR filter in the reverse model, so normally the forward model should have fewer parameters than the reverse model, $n_a > n_b$, for physical reasons.
- In the least squares method, the left hand side should be the variable that is observed with noise, while the other one should be noise-free. It is natural to assume that the brain has other tasks to solve than to process the sound, so there is clearly a large error in the EEG signal. The perceived sound also includes disturbances, which we model as the $n_u$ separate sound sources. These are arguments that favour the forward model. If there is noise on the regression vector, that is the Hankel matrices $\mathcal{H}(U_i)$ and $\overline{Y}_j$, respectively, then the total least squares method (TLS) should be used. This is computationally much heavier to implement. If TLS is not used, the parameters will be biased. A smaller bias in the forward model is thus expected.
- In theory, any b(t) polynomial should be accurately approximated with an a(t) polynomial in the reverse model. What we require is that the convolution b*a(t) $\approx \delta(\tau)$ is approximately a time-delayed impulse, or, in another words, that $\mathcal{H}(U_i)^\dagger \overline{Y}_j \approx I$ and $\overline{Y}_j^\dagger \overline{U}_i \approx I$. Solving this for a physical real FIR filter will almost certainly lead to an unstable a polynomial, since a random decently long FIR filter will have its zeros both inside and outside the unit circle.

C. Classification:

The loss function $V_{ij}(\hat{B}_{ij})$ gives a measure of model fit. The smaller value compared to the signal energy $V_{ij}(0) = \Sigma y_j^2(t)$ the better. Note that $V_{ij}(0)$ means no model at all. We should already here state that the model fit is very poor for this kind of application, compared to many other physical systems. The brain is processing a lot of other information, and the correlation to the sound sources is order of magnitudes smaller than its normal operations. However, for classification, the model fit is secondary and the primary purpose is to find the attended source. This can now be classified using arg $\min_i V_{ij}(\hat{B}_{ij})$, that is, the sound source that best explains the EEG signal.

If multiple EEG signals are used, which should be the case, then the total LS loss function is simply the sum over all channels, and the attended source is classified as $$\arg\min_i V_{ij}(\hat{B}_{ij}) \quad (9)$$

D. Sparse Modeling:

It is for physical reasons plausible that not all EEG channels and not all time delays in the model are useful for modeling the sound sources. For that purpose, we propose to add $l_1$ regularization to the $l_2$ LS cost function, and use $$V_i(B) = \Sigma_{j=1}^{n_y} \|Y_j - \mathcal{H}(U_i) B_j\|_2^2 + \lambda \|(B_1, B_2, \ldots, B_{n_y})\|_1 \quad (10)$$

where B is the total multiple output FIR filter $B = (B_1, B_2, \ldots, B_{n_y})$ for input i. The $l_1$ term is an approximation of the $l_0$ norm that simply counts the number of non-zero elements in the FIR filter B. That is, we seek a compromise between a good model fit and a sparse FIR filter with few parameters. The $l_1$ norm is used to get a convex problem, where efficient numerical solvers can be used. The parameter $\lambda$ is used to compromise sparseness to model fit.

ADMM reformulates the optimization problem into another one with different B vectors in the cost function, and an equality constraint, $$V_i(B) = \Sigma_{j=1}^{n_y} \|Y_j - \mathcal{H}(U_i) B_j\|_2^2 + \lambda \|\overline{B}\|_1 \quad (11)$$

subject to $\overline{B} = B$. (12)

The subtle point with this is that this trick enables a very efficient method. Basically, ADMM iterates between computing B, $\overline{B}$ and a third quantity, each step requiring simple calculations, and with, in practice, very fast convergence in only a few iterations.

There is also a group formulation of ADMM, where the penalty term is a sum of $l_l$ norms [24]. For this application, it can be used to select either the most relevant EEG channels, or the time instants where the combined EEG response is the most informative. To exploit such structured sparseness, the following norms may preferably be used:

- Use the row sum $\Sigma_{t=1}^{N} \|B_{t,:}\|_1$ to get a sparse time response.
- Use the column sum $\Sigma_{j=1}^{n_y} \|B_{:,j}\|_1$ to get a sparse EEG channel response.

The ADMM is described in more detail in the article by [Alickovic et al; to be published], which is attached to the present application and to which the above used equation numbers (1)-(12) refer.

Example:

An embodiment of a proposed solution to the 'sound source of interest identification in a multi-sound source environment' problem comprises five components, two of which (X1, X2) may be seen as preparatory steps aimed at understanding how the human auditory system reacts when exposed to different sound sources and attending to one of these sources:

X1. To identify dynamical effects of the speech on the brain and the relevance of each EEG channel, a FIR multiple input multiple output (MIMO) model from speech to EEG is formulated (to provide a physical insight into the model).

X2. To provide a sparse model that automatically selects the EEG channels and parameters of the FIR model, including time delay and model order k, of the highest relevance, an alternating direction of multipliers method (ADDM) is used.

A. To use this knowledge and attain a reliable model to precisely detect the single sound source of interest (under the requirement of real time identification) a causal model from speech to EEG with a reasonably long memory is necessary. A full FIR single input multiple output (SIMO) model for each speech stream is formulated, B. To get sparse models and to look for the model that best describes the data, the ADMM framework is used.

C. To determine the sound sources of the listener's interest cost functions of each model are compared.

These five components are further described in the following.

FIR MIMO Model Formulation (Component X1, X2)

A standard causal multivariate FIR model (FIR(k)) can be formulated as the following difference equation:

$$y_j(t) = b_{i,j,0} u_i(t) + b_{i,j,1} u_i(t-1) + \ldots + b_{i,j,k} u_i(t-k) + e_j(t) \quad (2)'$$

for $j=1, \ldots, n_y$, $i=1, \ldots, n_u$ and $t=1, \ldots, N$, where $e_j(t)$ is the disturbance and k is the order of the model. In general, $e_j(t)$ is considered to be white noise and $e_j(t) \sim N(0, \sigma_j^2)$. It is also assumed that $u_i(t)=0$ and $y_j(t)=0$ for $t<0$, which is a convenient way to ensure causality.

Formulated models will serve for different purposes and the amount of data used (N) corresponds to data from sliding window (the intended on-line application), one trial (model selection for one batch of one minute), all trials for one listener (subject-specific or individual model selection for all 30 minutes of data) or all trials for all subjects (grand-subject or global model selection). The data set $\Omega=\{u_1(1), u_2(1), y_1(1), \ldots, y_{128}(N)\}$ is the source of information we have at hand about the underlying actual system which needs to be fitted to model structure (2).

The first objective is to formulate FIR(k) MIMO model from each sound source i to each EEG channel j. Thus, the problem boils down to estimating $kn_u$ model parameters from each sound source from $Nn_y$ measurements. Model order k should be carefully chosen to include all time lags where speech signals may have a substantial influence on the EEG signals. Here, the main goal is to decide on the EEG channels and time-delays of the highest relevance. A simplistic approach to solve this problem would be to add $l_1$ regularization term to the simple least squares (LS), leading to ADMM, to get a more parsimonious model.

Eq. (2)' can be formulated in linear regression framework as $$y_j(t) = U_{i,j}^T(t) B_{i,j} + e_j(t) \tag{3}'$$

where $U_{i,j}(t)$ is a regression vector with elements $U^{(m)}_{i,j} = u_{i,j}(t-m)$, T denotes transposition, and $B_{i,j}$ is a function mapping stimulus $U_{i,j}(t)$ to neural response $y_j(t)$ with elements $B^{(m)}_{i,j} = b_{i,j,m}$ for $m=1, \ldots k$. For simplicity of the notation, the model (3)' can be generalized to one that explains all $n_u$ sound sources and $n_y$ EEG channels from a batch of N data as $$Y = UB + E \tag{4}'$$

where $$B = \begin{bmatrix} B_{1,1} & \cdots & B_{1,n_y} \\ \vdots & \ddots & \vdots \\ B_{n_u,1} & \cdots & B_{n_u,n_y} \end{bmatrix}$$

is a Hankel matrix, Y and E are $N \times n_y$ and U is $N \times k \cdot n_u$ matrices.

Once we have deeper understanding of the most informative EEG channels and time lags are selected, the next objective is to obtain the sparsest solution. As we aim to obtain a sparse B matrix, non-vanishing (non-zero) terms in B will give us which electrodes were active at each particular time lags, i.e., zero elements in B refer to inactive electrodes whereas non-zero elements refer to active electrodes. Thus B selects for the most important EEG-channels and time lags.

FIR SIMO Model Formulation (Component A, B)

The next objective is to estimate the full FIR SIMO model for each input source separately and attempt to select the model that explains data the best. This can be solved as a $l_1$ regularized least squares (LS) problem. Similar to the full FIR MIMO model in eq. (4)', the full FIR SIMO model for each input sound source can be generalized to a model that explains all $n_y$ EEG signals from a batch of N data as $$Y = U_i B_i + E \tag{5}'$$

where $B_i = [B_{i,1}, \ldots, B_{i,n_y}]$ is the Hankel matrix and $U_1$ is an $N \times k$ matrix.

Cost Minimization (Component C)

The $l_1$ regularized LS problem can be defined as:

$$\text{minimize } \{(\tfrac{1}{2}) \|Y - UB\|^2 + \lambda \|B\|_1\} \tag{6}'$$

The Frobenius norm $\|W\|^2 = \text{Trace}(W^T W)$ is used for matrix residual of the first term (model fit), Trace($\cdot$) being the sum of the diagonal elements of the argument matrix, and $$\|B\|_1 = \Sigma_{i,j,m} |b_{i,j,m}|.$$

The parameter $\lambda > 0$ is a regularization parameter set as the trade-off between model fit to the measurements u and y and model sparsity. Model defined in eq. (6)' is also known as the least
absolute shrinkage and selection operator (lasso) [26].

It should be noted that—in general—we do not attempt to estimate the covariance matrix of the EEG signals, but assume that they are independent signals that can be described by a stationary process with the same noise level $\sigma^2$. If, however, such a covariance matrix exists, the norm above is easily modified. The independence assumption allows to solve the least squares problem for each column of B separately, which saves a lot of computations.

It should further be noted that the term 'stimuli' refers to an input speech stream and these two terms will be used interchangeably when referring to the input signals $u_i$. It should also be noted that the 'response' refers to the output EEG signals and we will use them interchangeably when talking about the output signals $y_j$.

Model Estimation:

In following, mathematical tools that may be used to find a reliable model for attention selection are discussed. The $l_1$ regularized LS problem can be modified to a convex optimization problem and solved using standard methods for convex optimization such as CVX [9], [8] or YALMIP [15]. For large-scale $l_1$ regularized LS problems, special purpose-specific methods, such as PDCO [25] and l1-ls [10], were developed. We solve lasso problem (6) with ADMM, fast first order method, as alluded to previously.

A. Selection of Regularization Parameter $\lambda$.

The estimated parameter sequence $b_{i,j,m}$ as a function of $\lambda$ is called 'regularization path' for the problem (6)'. In general, as $\lambda$ decrease, model fit improves, but the pay-off is many non-zero elements and vice versa. The fundamental result of convex analysis states that $l_1$-regularized LS estimate must converge to zero valued estimates $b_{i,j,m}$ for some positive value of $\lambda$ if and only if $\lambda \geq \lambda^{max}$, i.e., $\lambda^{max}$ can be seen as threshold above which $b_{i,j,m} = 0$, $\forall (i, j, m)$. Hence, fraction of $\lambda^{max}$ is a sound start determining the 'best' value of $\lambda$. The $\lambda^{max}$ can be expressed as:

$$\infty > \lambda^{max} = \|U^T Y\|_\infty \tag{7}'$$

where $\|\kappa\|_\infty = \max_{i,j} |\kappa_{i,j}|$ denotes max norm ($l_\infty$) of $\kappa$.

To verify eq. (7)', the results from the convex analysis are used (cf. e.g. [11]). Let $$V_N = \tfrac{1}{2} \|Y - UB\|^2 + \lambda \|B\|_1 \tag{8}'$$

The objective function in eq. (6)' is convex, but not differentiable, and therefore, taking the sub-differential of (6)' with respect to B, we have $$\partial V_N = [U^T \cdot (UB - Y)]_{i,j,m} - \lambda \, \text{sign}(b_{i,j,m}) \tag{9}'$$

where sign(·) is defined component-wise as $$\text{sign}(\cdot) = \begin{cases} \{1\} & \text{if } b_{i,j,m} > 0 \\ \{-1\} & \text{if } b_{i,j,m} < 0 \\ [-1,1] & \text{if } b_{i,j,m} = 0 \end{cases}$$

Next, we note that the sub-differential eq. (9)' is a set. It follows readily from the optimality condition for convex programs, i.e., B is the optimal solution if and only if $0 \in \partial V_N$, that $(U^T Y)_{i,j,m} \in [-\lambda, \lambda]$ which yields $\lambda^{max} = \|U^T Y\|_\infty$. The sound choice for $\lambda$ is the fraction of $\lambda^{max}$, i.e., (in percent) $(0.01-1)\lambda^{max}$.

B. Lasso ADMM.

In ADMM form, lasso problem given in (6)' is as follows:

$$\text{minimize } \tfrac{1}{2}\|Y - UB\|^2 + \lambda \|\underline{B}\|_1 \text{ subject to } B = \underline{B} \quad (10)'$$

Augmented Lagrangian (AL) blends linear and quadratic terms as:

$$L_\rho(B, \underline{B}, \Delta) = \tfrac{1}{2}\|Y - UB\|^2 + \lambda \|\underline{B}\|_1 + (\rho/2)\|B - \underline{B} + \Delta\| \quad (11)'$$

where $\rho > 0$ is a penalty term and $\Delta$ is a scaled dual variable linked to constraint $B = \underline{B}$. In every iteration step it, ADMM minimizes AL over B and $\underline{B}$ separately with a single Gauss-Seidel pass. At iteration it, the following steps are carried out:

$$B^{it+1} = (U^T U + \rho I)^{-1}(U^T Y + \rho(\underline{B}^{it} - \Delta^{it})) \quad (12a)'$$

$$\underline{B}^{it+1} = S_{\lambda/\rho}(B^{it+1} + \Delta^{it}) \quad (12b)'$$

$$\Delta^{it+1} = \Delta^{it} + B^{it-1} - \underline{B}^{it+1} \quad (12c)'$$

where soft thresholding operator S is defined as $S_{\lambda/\rho}(\alpha) = (\alpha - \lambda/\rho)_+ - (-\alpha - \lambda/\rho)_+$. where + is a sub-script and $$(s)_+ = \begin{cases} s, & \text{if } s \geq 0 \\ 0, & \text{otherwise} \end{cases}.$$

The number of iterations needed for the algorithm to converge is greatly influenced by the selection of parameter $\rho$. With properly selected $\rho$, ADMM can converge to reasonably accurate model estimates within relatively few iteration steps and $\rho$ can be set to 1, i.e., $\rho = 1$.

We carry out iterations $it = 1, 2, \ldots$ in (12a)'-(12c)' until convergence or until termination criteria are met. Let $$\varepsilon^{it}_{prim} = B^{it} - \underline{B}^{it} \quad (13a)'$$

$$\varepsilon^{it}_{dual} = -\rho(\underline{B}^{it} - \underline{B}^{it-1}) \quad (13b)'$$

be primal and dual residuals at the it-th iteration. The algorithm is e.g. terminated when these two residuals satisfy stopping criteria that is usually $\varepsilon^{it}_{prim} = <\varepsilon^{prim}$ and $\varepsilon^{it}_{dual} = <\varepsilon^{dual}$ where $\varepsilon^{prim} > 0$ and $\varepsilon^{dual} > 0$ are feasibility tolerances set as $$\varepsilon^{prim} = \sqrt{kn_u}\varepsilon^{abs} + \varepsilon^{rel} \max\{\|B^{it}\|, \|\underline{B}^{it}\|\} \quad (14a)'$$

$$\varepsilon^{dual} = \sqrt{kn_u}\varepsilon^{abs} + \varepsilon^{rel} \rho\|\Delta^{it}\| \quad (14b)'$$

and $\varepsilon^{abs}$ and $\varepsilon^{rel}$ are the absolute and relative tolerances. ADMM is discussed in more details in [4].

C. Group Lasso ADMM.

The problem we have considered till now is given in (6)'. If the regularizer $\|\underline{B}\|_1$ is replaced with $$\sum_{t=1}^{kn_y} \|B_t\|_2$$

in the form $$\text{minimize } \tfrac{1}{2}\|Y - UB\|^2 + \lambda \sum_{t=1}^{kn_y} \|B_t\| \quad (15)'$$
$$\text{subject to } B = \underline{B}$$

where $\underline{B} = [\underline{B}_1, \underline{B}_2, \ldots, \underline{B}_{kn_y}]^T$. The problem (15)' is known as group lasso. It is easy to reformulate (15)' as:

$$\text{minimize } \tfrac{1}{2}\|Y - UB\|^2 + \lambda \sum_{t=1}^{kn_y} \|E_t B\| \quad (16)'$$

where $E_t$ is the t-th row in $I_{kn_y}$ (where $I_{kn_y}$ is the identity matrix of size $kn_y$).

ADMM for (15)' and (16)' is the same as for (10)' with $\underline{B}^{it}$ being replaced with block soft threshold as $$\underline{B}^{it+1}_t = S_{\lambda/\rho}(B^{it+1}_t + \Delta^{it}); \, t=1,2,\ldots,kn_u \quad (17)'$$

and soft threshold operator S is defined as $S_{\lambda/\rho}(\alpha) = (1 - \lambda/(\rho \cdot \|\alpha\|))_+ \alpha$ and subscript + refers to positive part of the expression, i.e, $$(s)_+ = \begin{cases} s, & \text{if } s \geq 0 \\ 0, & \text{otherwise} \end{cases} \text{ with } S_{\lambda/\rho}(0) = 0.$$

It can be noticed that (16)' enforces an entire row to be zero, which means that the resulting B is not necessarily sparse although it has entire zero rows. Roughly, with a single value $\lambda$, it is not always easy to find which rows are actually forced to be zero. It may hence be advantageous to use prior knowledge (is such knowledge is available) of probable zero rows, which may be (heuristically) enforced with the following reformulation of (16)' as:

$$\text{minimize } \tfrac{1}{2}\|Y - UB\|^2 + \lambda \sum_{i=1}^{kn_y} \|E_i B\|_2 \quad (18)'$$

where significantly larger values of $\lambda_i$ are given to those rows.

EEG Channel and Model Order Selection with MIMO FIR Model

In following, the dynamical effects of the brain in relation to the present multi-source acoustic stimulation scenario are discussed. To get physical insight, the ADMM is applied with the aim of identifying the EEG channels and time-delays of the highest relevance. What remains now is to decide on a suitable regularization parameter $\lambda$ so that the model fit is satisfactory while the number of zero elements is kept fairly high. Low sparsity is computationally forbidding for larger k values. Once, a suitable $\lambda$ has been selected, model dynamics can be analysed.

From a more pragmatic point of view, it is now relatively easy to observe which electrodes are active at which time lags and duration of sound effect(s) on the brain. This knowledge can typically be incorporated into separating out the sound source of interest from the other sources and solving the cocktail party problem.

An interesting outcome of the sparse data is connectivity. The electrodes are only picking up what is happening on the surface of the brain, but neurons may actually be connected at deeper levels. So sparse events close in time but physically separated may be connected. Thus, with sparsity, we may get insight into deeper levels and how different connections and layers communicate to each other.

We will use the amount of data N corresponding to all trials for each listener, that is N~30 trials×60 seconds×64 Hz, as a vehicle for selecting relevant EEG electrodes and time delays for understanding speech representation in the brain.

CLASTIC: CLassification of Attended speech STream In Cocktail-party Problem.

To (possibly) solve the cocktail party problem is now to perform LS estimation for each FIR SIMO model in (10)' and see which input signal gives the smallest cost. Put simply, to estimate $B_i$ for n-th batch is only needed to compute the cost function at the minimum $$\hat{V}_N^i(n) = \tfrac{1}{2}\|Y - U_i B_i\|^2 + \lambda \|\underline{B}_i\|_1 \tag{19}'$$

Then, the (possible) approach to determine the sound source attended to by the user can be $$\hat{i} = \arg\min_i \hat{V}_N^i(n) \tag{20}'$$

A related approach to identify the sound source $\hat{i}$ (denoted $\hat{S}_i$ or $\hat{S}_x$ in connection with the drawings) attended to by the user may be to use the moving average (MA(p)) of the loss functions. Then $$\hat{V}_{MA}^i(k) = \sum_{i=0}^{p-1} \hat{V}_N^i(n-i) \tag{21}'$$

$$\hat{i} = \arg\min_i \hat{V}_{MA}^i(k) \tag{22}'$$

Where the index k is the model order, i.e., the number of time lags considered in the model. What is meant by (21)' is that we can have the first decision on the attended sound source after p batches. As an example, consider batches of one minute each and let p be 10. In this case we have first decision after 10 minutes and decisions are updated each minute afterwards.

Model Order k.

In the following some guidelines for selecting the model order k (cf. FIR(k)), that is, the number of parameters or time lags when formulating the model in (2)' are provided. A penalty function can be added to simple LS to find the true model order k* to avoid over-learning. Intuitive advice is to use the regularized criterion since regularization parameter $\lambda$ can be thought of as a "knob" that we use to curb the effective number of parameters in the model, without being forced to decide which parameters should vanish, but letting the criterion (8)' to use the time lags that influence the model fit the most. Thus, when the number of parameters k is unknown, $\lambda$ can be used as the trade-off between model fit and model order. Since $l_1$ regularization introduces sparsity and the adequate freedom is needed to describe the true system so that we can understand how the speech is represented within the brain, we evaluate the model of higher order, that is, we set $k = 5 \times F_S = 320$ (5 seconds prior to time t, $t = 1, 2; \ldots, N$), where $F_S$ is the sampling frequency ($F_S = 64$ Hz).

The filters $\underline{B}$, $\underline{B}_1$ and $\underline{B}_2$ are rightly to be considered as spatial filters, mapping the stimuli signal (speech stream) to response signal (EEG signals) at each time lag.

Individual Model Selection (N=30 min)

We first introduce experimental results for individual model selection for all 30 minutes of data for each subject. Regularization parameter $\lambda$ is selected so that the cost (see Eq. (20)') for the attended speech stream is smaller when compared to the cost for the unattended speech stream.

The (estimated) sparse filters $\underline{B}$ for FIR MIMO model in Eq. (4)' give us the filter weights $B^{(m)}_{i,j}$ across the scalp for each individual time-lag m. This formulation is suitable for jointly tracking two competing speech streams in the left and right ear. Sparsity introduced with ADMM gives us the "most active" electrodes at each individual time lag where the "most active" electrodes will possibly indicate the neurons connected at deeper levels across the higher order auditory cortex. This gives us the deeper insight into dynamic properties of the human auditory system and the ability to track the sound within the brain and see brain parts being highly excited by stimuli at each particular point in time. With such an approach, we can better understand how the auditory system extracts intelligible speech features in acoustically complex backgrounds.

The filter $\underline{B}$ can (possibly) explain neural encoding mechanism jointly with the feedbacks and also the brain's mechanism for solving the cocktail-party problem. When $B^{(m)}_{i,j}$ is analysed separately for each time-lag and for each subject, dynamics can be identified. It can be seen that the electrodes were the most active or the most sensitive to speech streams up to FIR filter order of 60, what corresponds to response fading after approximately 1 second.

To confirm this impression, we averaged the filters $\underline{B}^s$ over all subjects, $s = 1, 2, \ldots, 10$, so that all non-vanishing (nonzero) filter weights for all subjects can be inspected together. From the "average" filter it can be verified that most of the neural processes occur for both speeches during the first 60 time lags.

Attentional modulation was also further investigated and quantified for the attended and unattended speech streams separately. A related question is if the data set $\Omega$ allows us to distinguish between different models given by filters $B_1$ and $B_2$, see Eq. (5)'. Two SIMO FIR models were formulated from data set $\Omega$ for two different speech streams and filters $\underline{B}_1$ and $\underline{B}_2$ were computed for each subject. We call a data set $\Omega$ informative if we can distinguish between the highly structured patterns of filters $\underline{B}_1$ and $\underline{B}_2$[14]. This finding allows us to visualize and gain deeper understanding of how the different competing speech streams are encoded in the brain. The primary difference between $\underline{B}_1$ and $\underline{B}_2$ is evident when plotted separately for each time lag what confirms that data set $\Omega$ is informative or contains relevant information about the dynamics of speech streams and their differences in highly structured patterns.

To investigate what properties the sequence of filters $\{\underline{B}_1\}^s_t$ and $\{\underline{B}_2\}^s_t$ may have, we further examined the average across the subjects for $\underline{B}_1$ and $\underline{B}_2$ separately for all time lags $t = 1, 2, \ldots, N$ and all subjects $s = 1, 2, \ldots, 10$. Averaging the filters $\underline{B}_1$ and $\underline{B}_2$ over time and subjects, say, $$\sum\nolimits_1 = \frac{1}{S}\sum_{s=1}^{S} B_1^s \tag{23}'$$

$$\sum\nolimits_2 = \frac{1}{S}\sum_{s=1}^{S} B_2^s \tag{24}'$$

gives the fair picture of which EEG channels and time lags have been captured in the underlying system.

The insight of the present disclosure points towards that the EEG electrodes are the most active in the first second following the stimuli. This may represent the processes at higher order auditory cortex. This also confirms that dataset Ω is informative enough to distinguish between filters $B_1$ and $B_2$ and thus to identify the attended speech stream.

In an embodiment, a feed filter B is obtained with an ADMM to linear support vector machine (SVM) algorithm ($Y=U_i*B_i$, where $U_i$=sound signals, Y=EEG signals).

Figure 2A:
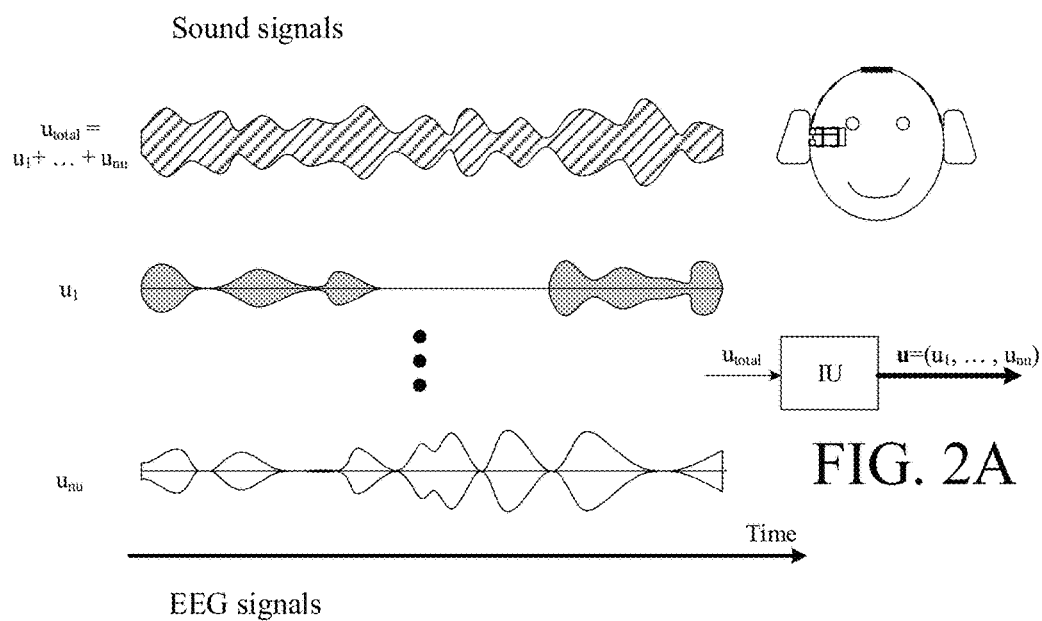
FIG. 2A illustrates (in the lower part) schematic time segments of (envelopes) of sound signals $u_i$, i=1, ..., $n_u$, of currently active sound sources $S_i$ of FIGS. 1C, 1D as provided by a sound source separation unit (SSU) of the hearing assistance system, and (in the upper part) a mixture $u_{total}$ of said sound signals as received by a hearing device at an ear of the user.

FIG. 2A illustrates (in the lower part) schematic time segments of (envelopes) of sound signals $u_i$, i=1, . . . , $n_u$, of currently active sound sources $S_i$ of FIGS. 1A-1J as provided by a sound source separation unit (SSU) of the hearing assistance system, and (in the upper part) a mixture $u_{total}$ of said sound signals as received by an input unit (IU, e.g. in a hearing device) at an ear of the user.

Figure 2B:
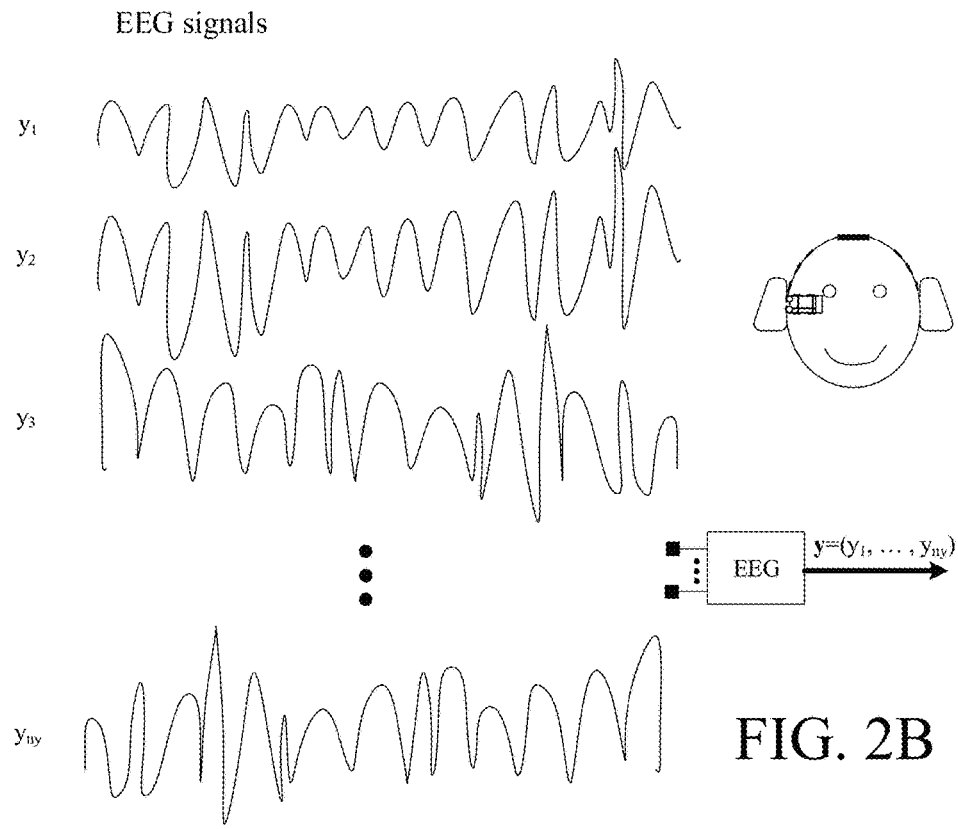
FIG. 2B illustrates schematic time segments of corresponding EEG signals $y_1, y_2, ..., y_{ny}$, evoked by the mixed sound signal $u_{total}$ and as picked up by a number $n_y$ of EEG-electrodes and provided by an EEG system of an embodiment of a hearing assistance system according to the present disclosure comprising a multi-microphone unit, a sound source separation unit, and an EEG system.

FIG. 2B illustrates schematic time segments of corresponding EEG signals $y_1, y_2, \ldots, y_{ny}$, evoked by the mixed sound signal $u_{total}$ and as picked up by a number $n_y$ of EEG-electrodes and provided by an EEG system of an embodiment of a hearing assistance system according to the present disclosure comprising a multi-sound input unit, a sound source separation unit, an EEG system, and a sound source selection unit.

The time line (bold arrow denoted 'Time') separating FIG. 2A from FIG. 2B is intended to indicate the coincidence in time of the mixed sound signal(s) $u_{total}$, the separated sound signals $u_i$ and the EEG signals $y_j$.

Figure 3:
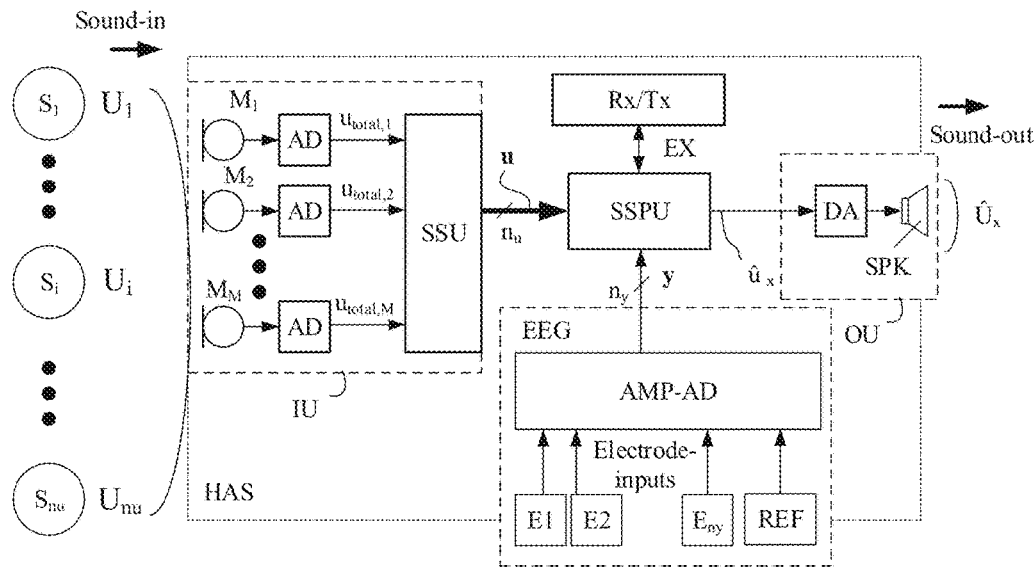
FIG. 3 shows a first further embodiment of a hearing assistance system according to the present disclosure.

FIG. 3 shows an embodiment of a hearing assistance system according to the present disclosure in a sound environment as illustrated in FIGS. 1A-1J. The hearing assistance system comprises an input unit (IU) for providing electric input sound signals $u_i$, i=1, . . . , $n_u$ (denoted u in FIG. 3), each representing sound signals $U_i$, from a multitude $n_u$ of sound sources $S_i$ (i=1, . . . , $n_u$) (bold arrow denoted 'Sound-in' in FIG. 3), an electroencephalography system (EEG) for recording activity of the auditory system of the user's brain and providing a multitude $n_y$ of EEG signals $y_j$ (j=1, . . . , $n_y$) (denoted y in FIG. 3), and a source selection processing unit (SSPU) coupled to the input unit (IU) and to the EEG-system (EEG) and receiving the electric input sound signals u and the EEG signals y. The source selection processing unit (SSPU) is configured—in dependence of signals u and y—to provide a source selection signal $\hat{S}_x$ indicative of the sound source $S_x$ that the user currently pays attention to. Based thereon, the source selection processing unit (or a processing unit in communication therewith) is configured to estimate an audio signal $\hat{u}_x$ representative of the sound signal $U_x$ that the user currently pays attention to. The hearing assistance system further comprises an output unit (OU) for providing stimuli representative of the sound signal $U_x$ based on the (electric) audio signal $\hat{u}_x$ from the source selection processing unit (SSPU). The input unit (IU) comprises a number of input transducers, here microphones (denoted $M_m$), m=1, . . . , M, each for providing an analogue input electric signal representing environment sound. In general M can be any appropriate number, e.g. one or more, e.g. two or more. The input unit (IU) further comprises a number of analogue to digital converters (AD) for converting said analogue input electric signals to digital electric input signals $u_{total,m}$, m=1, . . . , M, each representing a mixture of sound signals as received at the location of the input transducer $M_m$ in question. The input unit (IU) further comprises a source separation unit (SSU) for separating the electric input signals $u_{total,m}$, m=1, . . . , M, and providing (estimates) of the separated electric input sound signals u ($u_i$, i=1, . . . , $n_u$). The source separation unit (SSU) may e.g. comprise a beamforming algorithm in addition to a source separation algorithm, the latter preferably exhibiting a relatively low delay (e.g. less than 50 ms, such as less than 20 ms). The output unit (OU) comprises digital to analogue conversion unit (DA) for converting the (digital, electric) audio signal $\hat{u}_x$ to an analogue output signal and an output transducer (SPK) in the form for a loudspeaker for converting the analogue electric audio signal $\hat{u}_x$ to an output sound signal $\hat{U}_x$. The EEG system (EEG) comprises a number of electrodes $E_j$ (j=1, . . . , $n_y$) and a reference electrode REF. The potentials picked up by the electrodes ('Electrode inputs' in FIG. 3) are fed to the amplifier and analogue to digital conversion unit (AMP-AD), which provides $n_y$ amplified, digital EEG-signals y to the source selection processing unit (SSPU). The hearing assistance system (HAS) further comprises transceiver circuitry (Rx/Tx) for exchanging information with another device, e.g. an auxiliary device or a hearing device (cf. signal EX between the source selection processing unit (SSPU) and the transceiver circuitry (Rx/Tx).

Figure 4A:
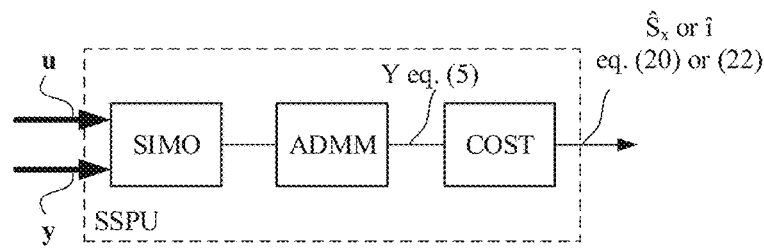
FIG. 4A shows a first embodiment of a source selection processing unit according to the present disclosure.

A source selection processing unit (SSPU) according to the present invention is coupled to an input unit (cf. IU in FIG. 3) and to an EEG-system (cf. EEG in FIG. 3) and receives as inputs the electric input sound signals $u_i$ (i= 1, . . . , $n_u$, =u in FIG. 3) and the EEG signals $y_j$, (j= 1, . . . , $n_y$, =y in FIG. 3) and in dependence thereof is configured to provide a source selection signal $\hat{S}_x$ indicative of the sound source $S_x$ that the user currently pays attention to. This is illustrated in FIG. 4A showing a first embodiment of a source selection processing unit (SSPU) according to the present disclosure. The source selection processing unit is configured to analyze the electric input sound signals $u_i$, i=1, . . . , $n_u$, and the multitude of EEG signals $y_j$, j= 1, . . . , $n_y$, using a selective algorithm that determines a sparse model to select the most relevant EEG electrodes and time intervals based on minimizing a cost function measuring the correlation between the sound source and the EEG signals, and to determine the source selection signal $\hat{S}_x$ indicative of the sound source $S_x$ that the user currently pays attention to based on the cost function obtained for said multitude of sound sources. This is e.g. performed as described above using a (e.g. full FIR) single input multiple output (SIMO) unit wherein a model for each speech stream is formulated, an alternating direction of multipliers method (ADMM) unit providing a sparse model that automatically selects the EEG channels (and optionally FIR parameters) of the highest relevance. To determine the sound source(s) $S_x$ of the listener's interest, a cost unit (COST) is used to compare cost functions of each model. In case one source is selected, the source can be represented by its index i (or estimated index $\hat{i}$).

Figure 4B:
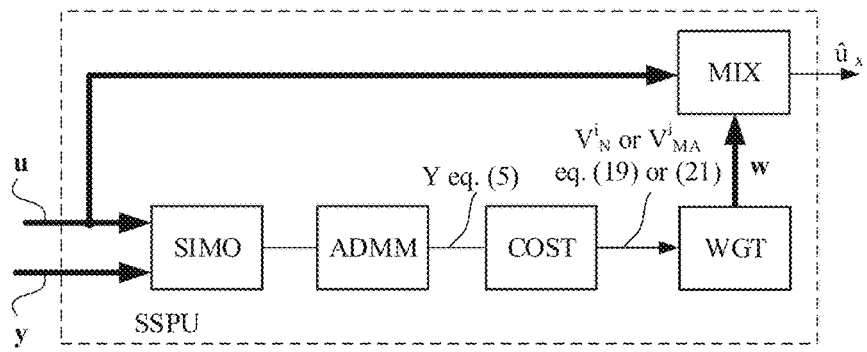
FIG. 4B shows a second embodiment of a source selection processing unit according to the present disclosure.

FIG. 4B shows a second embodiment of a source selection processing unit (SSPU) according to the present disclosure. The embodiment of FIG. 4B is equivalent to the embodiment of FIG. 4A apart from the weighting unit (WGT) that is inserted after the cost unit (COST). The weighting unit receives as inputs cost functions for at least some (such as a majority or all) of the electric input signals $u_i$, and provides based thereon (and on a possible predefined criterion or criteria) weights $w_i$ (i=1, . . . , $n_y$) (vector w) which are (at least to a certain extent) representative of the user's current attention to the available sound source signals. The weights $w_i$ are multiplied on the electric input sound signals $u_i$ and subsequently mixed in mixing unit (MIX) to provide a currently preferred mixture $\hat{u}_x$ of the sound signals. Such mixture is likewise provided by the sound source processing unit of FIG. 3. In an embodiment, a single sound source $u_x=u_i$ (i=one of 1, ..., $n_u$) is selected (so that all weights other than one is zero). In an embodiment, all other weights than the one corresponding to a preferred sound source are associated with a low weight smaller than a threshold value (to allow other sources than the one (estimated to be) of current interest to the user to be perceivable by the user).

Figure 5:
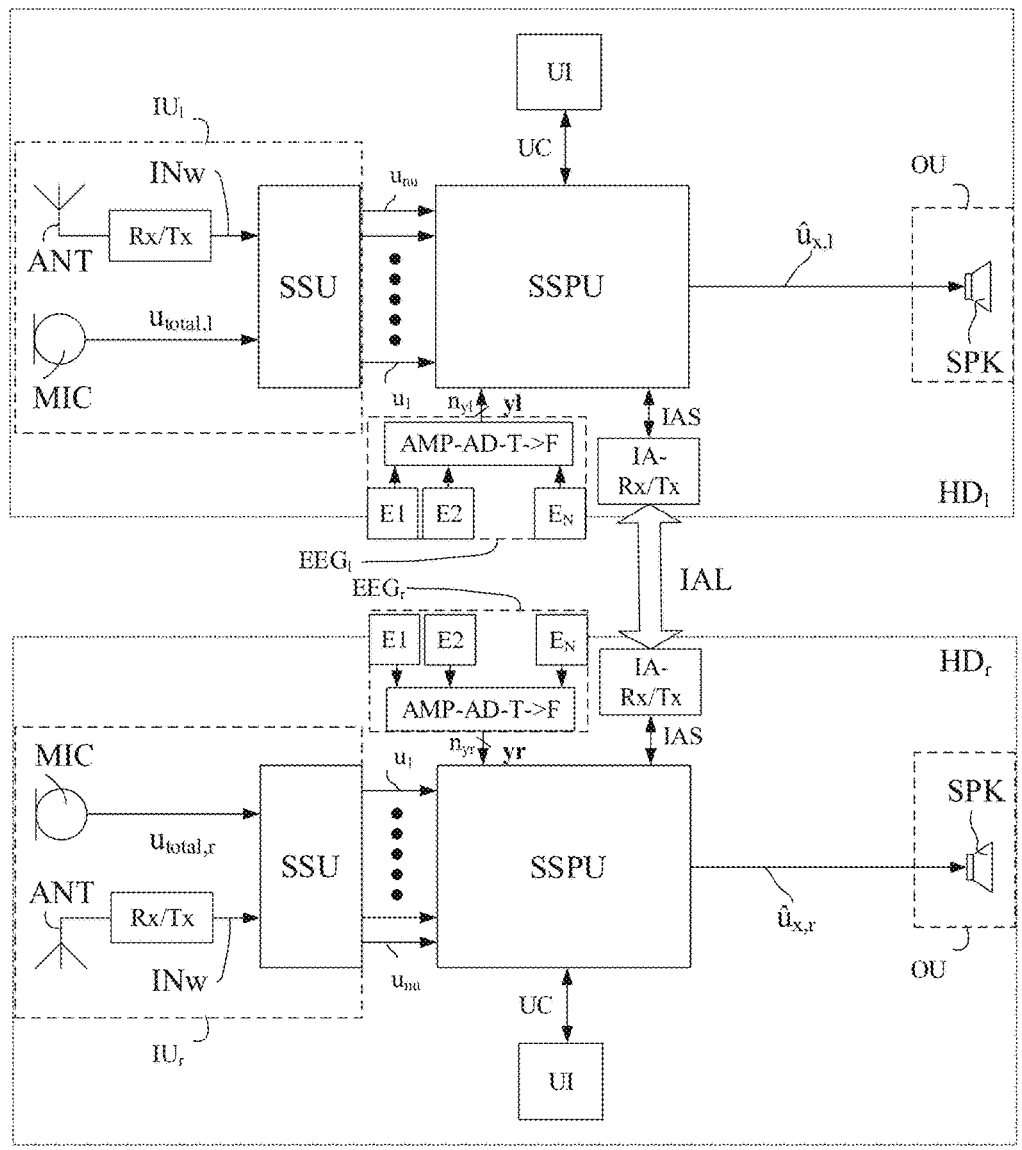
FIG. 5 shows an embodiment of a hearing assistance system according to the present disclosure comprising left and right hearing devices.

FIG. 5 shows an embodiment of a hearing assistance system according to the present disclosure comprising left and right hearing devices ($HD_l$, $HD_r$). The hearing assistance system of FIG. 5 comprises the same functional units as shown in and described in connection with FIGS. 1G and 1H. The left and right hearing devices of FIG. 5 may (each) e.g. be based on the embodiment of a hearing device as shown in FIG. 3. Compared to FIG. 3, the input units ($IU_l$, $IU_r$) of the left and right hearing devices additionally comprises antenna and transceiver circuitry (ANT, Rx/Tx) for receiving a wireless signal INw (e.g. comprising an audio signal, e.g. from an input transducer (e.g. a microphone) located separately from the hearing device in question). The wirelessly received signal may comprise a mixture of the currently active sound sources $S_i$ around the hearing device, or may contain a single one of the sound sources (e.g. from a wireless microphone at the mouth of a speaker), or may comprise substantially only a background noise signal, etc. The wireless signal INw is fed to the source separation unit (SSU) together with the mixed signal $u_{total,l}$ or $u_{total,r}$ (as the case may be), and optionally used in the source separation unit to provide separated electric sound source signals $u_i$, i=1, ..., $n_u$. In FIG. 5, only one microphone (MIC) is indicated in the respective input units. The input units ($IU_l$, $IU_r$) may, however, comprise more than one microphone (as illustrated in FIG. 3). The AD and DA converters of the input and output units of the embodiment of a hearing device shown in FIG. 3 are not shown in FIG. 5, but assumed to be present, as necessary. The hearing assistance system is configured to exchange one or more of the respective source selection signal $\hat{S}_{x,l}$, $\hat{S}_{x,r}$ indicative of the sound source $S_x$ that the user currently pays attention to, the respective electric input sound signals $u_{ir}$, $u_{il}$ ($u_l$, $u_r$) and the respective EEG signals $y_{jl}$, $y_{jr}$ ($y_l$, $y_r$) between the left and right hearing devices via interaural link IAL. The signals exchanged between the left and right hearing assistance devices ($HD_l$, $HD_r$) are communicated via (bi-directional) signal IAS between the respective source signal processing units (SSPU) and interaural transceiver units (IA–Rx/Tx). The hearing assistance system, including the left and right hearing assistance devices, further comprises a user interface (UI) to allow a user to control functionality of the hearing assistance system, e.g. for activating different modes of operation (e.g. programmes), for identifying a direction to a sound source of current interest to the user, to initiate an identification of the sound source of current interest to the user (based on evoked EEG-potentials), etc., cf. e.g. FIG. 6.

Figure 6:
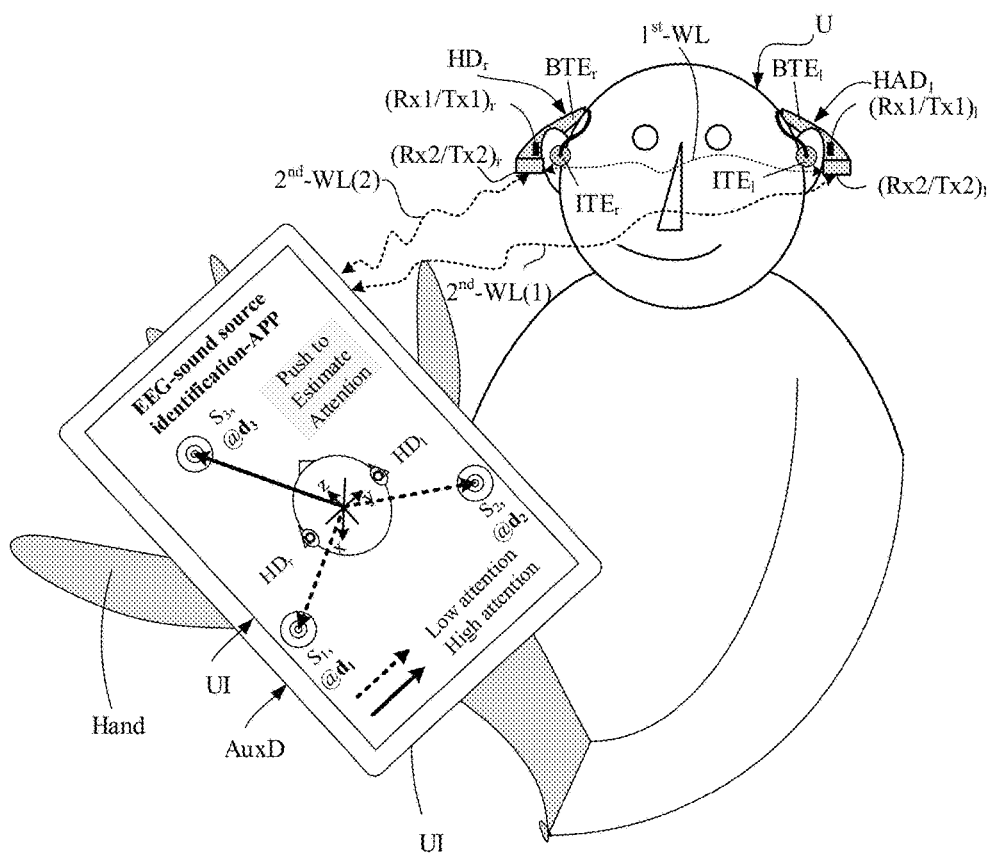
FIG. 6 shows an embodiment of a hearing assistance system according to the present disclosure comprising first and second hearing devices in communication with an auxiliary device functioning as a user interface for the hearing assistance system.

FIG. 6 shows an embodiment of a hearing assistance system comprising left (first) and right (second) hearing devices ($HD_l$, $HD_r$) in communication with a portable (handheld) auxiliary device (AuxD), e.g. a remote control or a SmartPhone, functioning as a user interface (UI) for the hearing assistance system. Each of the first and second hearing devices ($HD_l$, $HD_r$) comprises a BTE- and an ITE-part adapted for being located behind and in an ear, respectively of the user, and e.g. electrically connected via a connecting element. The first and second ITE-parts ($ITE_l$ and $ITE_r$, respectively, in FIG. 6) and/or the first and second BTE-parts ($BTE_l$ and $BTE_r$, respectively, in FIG. 6) comprise EEG and reference electrodes as discussed in connection with FIG. 1 to FIG. 5. The first and second BTE- and/or ITE-parts may further (each) e.g. comprise one or more input transducers, and an output transducer. In an embodiment, the BTE-parts (and the connecting elements) are dispensed with, so that all functionality of the hearing devices ($HD_l$, $HD_r$) is located in the respective ITE-parts ($ITE_l$, $ITE_r$). The first and second BTE-parts ($BTE_l$, $BTE_r$ in FIG. 6) may e.g. comprise a battery, one or more input transducers, a signal processing unit and wireless transceivers. In an embodiment, first and second BTE-parts ($BTE_l$, $BTE_r$) each comprise an output transducer and the attached first and second connecting elements each comprise an acoustic conductor, e.g. a tube, for propagating sound from the output transducer of a BTE-part to the corresponding ITE-part (and thus to the ear drum of the ear in question). In an embodiment, the hearing assistance system comprises the auxiliary device (AuxD and the user interface UI) and is e.g. configured to display information related to the system, e.g. to the measurement and analysis of the EEG-signals, e.g. an estimate of which of the multitude of sound sources (here $S_1$, $S_2$, $S_3$) that the user is most likely trying to listen to, and possibly an estimate of its location relative to the user (cf. FIG. 6, lower part). The user interface displaying information of the hearing assistance system may be implemented as an APP of the auxiliary device (e.g. a SmartPhone). In the embodiment of FIG. 6, the available wireless links are denoted $1^{st}$-WL (e.g. an inductive link between the hearing devices) and $2^{nd}$-WL(1) and $2^{nd}$-WL(2) (e.g. RF-links between the auxiliary device and the left and between the auxiliary device and the right hearing device, respectively). The $1^{st}$ and $2^{nd}$ wireless interfaces are implemented in the left and right hearing devices ($HD_l$, $HD_r$) by antenna and transceiver circuitry (($Rx1/Tx1)_l$, $(Rx2/Tx2)_l$) and (($Rx1/Tx1)_r$, $(Rx2/Tx2)_r$), respectively. The auxiliary device (AuxD) comprising the user interface (UI) is adapted for being held in a hand (Hand) of a user (U), and hence convenient for displaying information to the user and to be used by the user for controlling the system. The APP EEG-sound source identification-APP displays currently present sound sources ($S_1$, $S_2$, $S_3$) and their estimated localization ($d_1$, $d_2$, $d_3$) relative to the user (U). By correlating the captured EEG signals and the individual, currently present sound source signals (as e.g. provided by a source separation algorithm of the hearing device), sound sources having a correlation with the EEG signals below a predefined threshold value are denoted with 'Low attention' (dotted arrow, here sources $S_1$, $S_2$) and sound sources having a correlation with the EEG signals above a predefined threshold value are denoted with 'High attention' (full line arrow, here source $S_3$). The correlation is e.g. determined by a causal forward FIR-model from speech to EEG according to the present disclosure. Such information may be used to automatically and/or manually bring beamformers of the first and second hearing devices ($HD_l$, $HD_r$) to focus on the sound source ($S_3$) having the relatively higher correlation with the EEG signals. Thereby an improved perception (e.g. intelligibility of speech) of sound in a multi-sound source environment may be provided according to a users' will. An alternative scheme for (automatic) correlation of brainwave signals and current sound source signals is e.g. dealt with in US2014098981A1, wherein coherence between the measured brainwaves and an audio signal picked up by and processed by a forward path of the hearing device is determined. A re-calculation of the current sound source having the user's attention can be initiated via the EEG-sound source identification-APP by pressing the 'screen button' Push to Estimate Attention in the upper right part of the exemplary screen of the APP displayed by the user interface (UI) in FIG. 6. A manual selection of a sound source (e.g. $S_2$) currently having the attention of the user (thereby overriding the automatically determined source $S_3$) may e.g. be performed via the user interface (UI), e.g. by touching the source in question (e.g. $S_2$) on the display. The determination of the sound source of current interest of the user based on audio signals and brainwave signals may e.g. be performed in the respective hearing devices and the results transmitted to the auxiliary device for comparison (evaluation) and display. Alternatively, the calculations may be performed in the auxiliary device to save power in the hearing devices.

Figure 7A:
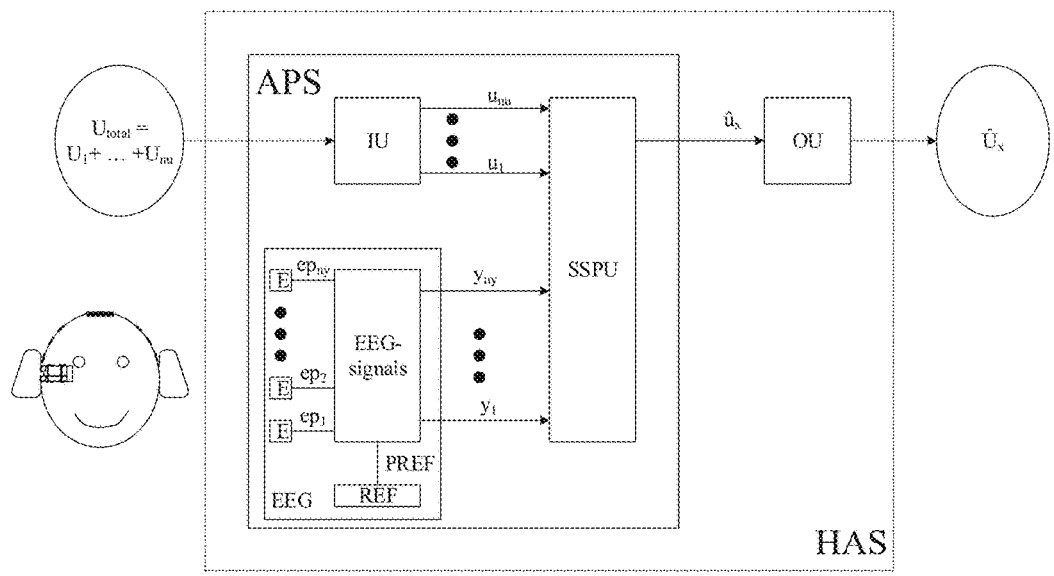
FIG. 7A shows a second further embodiment of a hearing assistance system according to the present disclosure.

FIG. 7A shows a second further embodiment of a hearing assistance system according to the present disclosure. The hearing assistance system shown in FIG. 7A comprises the same functional elements (IU, EEG, SSPU, OU) as described above, e.g. in connection with FIGS. 1C and 1D. The EEG system comprise a number $n_y$ of electrodes (E) each adapted for picking up a potential $ep_i$ (i=1, ..., $n_y$) from the user's brain and a reference electrode (REF) for picking up a reference potential PREF for use in generating EEG signals $y_i$ (from the respective potentials $ep_i$ (i= 1, ..., $n_y$), cf. unit EEG-signals in FIG. 7A.

Figure 7B:
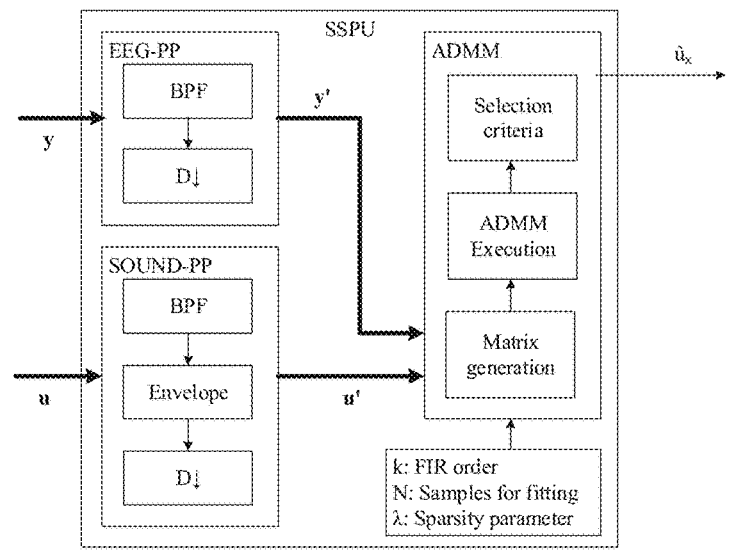
FIG. 7B shows a third embodiment of a source selection processing unit according to the present disclosure.

FIG. 7B shows a third embodiment of a source selection processing unit (SSPU) according to the present disclosure. The source selection processing unit (SSPU) receives the electric input sound signals $u_i$ (i=1, ..., $n_u$) from input unit IU in FIG. 7A (signals $u_i$ being denoted u in FIG. 7B) and the (e.g. raw) EEG signals $y_j$, (j=1, ..., $n_y$) from the EEG unit in FIG. 7A (signals $y_i$ being denoted y in FIG. 7B). The EEG input signals are processed in unit EEG-PP comprising respective band pass filtering units (BPF) for extracting the essential parts of the EEG signals y associated with brain activity (e.g. to frequencies below 20 Hz, e.g. between 1 Hz and 8 Hz). The band pass filtered EEG signals are down sampled in respective down sampling units (D1), e.g. to a frequency below 500 Hz, e.g. below 200 Hz, e.g. to 64 Hz, and provided as processed EEG signals y'. Similarly, the electric input sound signals u are processed in unit SOUND-PP comprising respective band pass filtering units (BPF) for extracting the essential parts of the sound signals y associated with brain activity. An envelope (e.g. a provided by a Hilbert transform of the band pass filtered signals) of the band pass filtered sound signals is extracted by unit Envelope, and the resulting envelope signals are down sampled in respective down sampling units (D1), e.g. to a frequency below 500 Hz, e.g. below 200 Hz, e.g. to 64 Hz, and provided as processed sound signals u'.

The processed EEG and sound signals (y', u') are fed to the alternating direction of multipliers method unit (ADMM) where the data are processed to generate appropriate matrices of relevance for the ADMM procedure (cf. e.g. eq. (2)-(12) above) and executed in unit ADMM Execution. The receiving further inputs regarding order k of the FIR filters, the number of samples N of the input signals, and the sparsity parameter $\lambda$ (cf. e.g. eq. (10)-(12) above). The sound source $S_x$ that the user currently pays attention to is determined based on chosen selection criteria (cf. unit Selection criteria), e.g. cost function(s)), applied to the output of the ADMM Execution unit. The further inputs (k, N, $\lambda$) are e.g. derived from learning data (e.g. in a learning mode of operation) or otherwise selected in advance and stored in a memory of the hearing assistance system. The sound source selection unit is (e.g.) configured to provide an estimate of the sound signal $U_x$ (from sound source $S_x$) that the user currently pays attention to, cf. (electric) output signal $u_x$ in FIG. 7B.

It is intended that the structural features of the systems and devices described above, either in the detailed description and/or in the claims, may be combined with steps of the method, when appropriately substituted by a corresponding process. Further details of the ideas presented in the present disclosure are given in the article by [Alickovic et al; to be published], which is attached to the present application and intended to constitute an appendix to be consulted for further details, if necessary.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[4] Stephen Boyd, Neal Parikh, Eric Chu, Borja Peleato, and Jonathan Eckstein. Distributed optimization and statistical learning via the alternating direction method of multipliers. Found. Trends Mach. Learn., 3(1):1-122, January 2011.

[8] Michael Grant and Stephen Boyd. Graph implementations for nonsmooth convex programs. In V. Blondel, S. Boyd, and H. Kimura, editors, Recent Advances in Learning and Control, Lecture Notes in Control and Information Sciences, pages 95-110. Springer-Verlag Limited, 2008.

[9] Michael Grant and Stephen Boyd. Cvx: Matlab software for disciplined convex programming, version 2.1, March 2014.

[10] Seung-Jean Kim, K. Koh, M. Lustig, S. Boyd, and D. Gorinevsky. An interior-point method for large-scale l1-regularized least squares. Selected Topics in Signal Processing, IEEE Journal of, 1(4):606-617, December 2007.

[11] Seung-Jean Kim, K. Koh, M. Lustig, S. Boyd, and D. Gorinevsky. An interior-point method for large-scale l1-regularized least squares. Selected Topics in Signal Processing, IEEE Journal of, 1(4):606-617, December 2007.

[14] Lennart Ljung. System Identification: Theory for the User. Prentice Hall PTR, Upper Saddle River, N.J. 07458, 2nd edition, 1999.

[15] J. Löfberg. Yalmip: A toolbox for modeling and optimization in MATLAB. In

Proceedings of the CACSD Conference, Taipei, Taiwan, 2004.

[16] T. Lunner and F. Gustafsson. Hearing device with brainwave dependent audio processing, Apr. 10, 2014. U.S. patent application Ser. No. 14/048,883, published as US20140098981A1.

[17] T. Lunner and N. H. Pontoppidan. Configurable hearing instrument, Jun. 19, 2014. U.S. patent application Ser. No. 14/103,399, published as US20140169596A1.

[18] Thomas Lunner. Hearing device with external electrode, Mar. 3, 2015. U.S. Pat. No. 8,971,558.

[21] James A. O'Sullivan, Alan J. Power, Nima Mesgarani, Siddharth Rajaram, John J. Foxe, Barbara G. Shinn-Cunningham, Malcolm Slaney, Shihab A. Shamma, and Edmund C. Lalor. Attentional selection in a cocktail party environment can be decoded from single-trial eeg. Cerebral Cortex, 25(7):1697-1706, 2015.

[23] N. H. Pontoppidan, T. Lunner, M. S. Pedersen, L. I. Hauschultz, P. Koch, G. Naylor, and E. B. Petersen. Hearing assistance device with brain computer interface, Dec. 18, 2014. U.S. patent application Ser. No. 14/303, 844, published as US20140369537A1.

[24] Alan J. Power, John J. Foxe, Emma-Jane Forde, Richard B. Reilly, and Edmund C. Lalor. At what time is the cocktail party? a late locus of selective attention to natural speech. European Journal of Neuroscience, 35(9):1497-1503, 2012.

[25] Michael Saunders. Pdco: Primal-dual interior method for convex objectives, October 2002.

[26] Robert Tibshirani. Regression shrinkage and selection via the lasso. Journal of the Royal Statistical Society, Series B, 58:267-288, 1994.

[Alickovic et al.; to be published] Emina Alickovic, Carina Graversen, Thomas Lunner, Fredrik Gustafsson, A sparse estimation approach to modeling listening attention from EEG signals. To be published.

[Bell and Sejnowski, 1995] Bell, A. J. and Sejnowski, T. J. *An information maximisation approach to blind separation and blind deconvolution*. Neural Computation 7(6): 1129-1159. 1995.

[Boldt et al., 2008] Boldt, J. B., Kjems, U., Pedersen, M. S., Lunner, T., and Wang, D. *Estimation of the ideal binary mask using directional systems*. IWAENC 2008. 2008.

[Jourjine et al., 2000] Jourjine, A., Rickard, S., and Yilmaz, O. *Blind separation of disjoint orthogonal signals: demixing N sources from 2 mixtures*. IEEE International Conference on Acoustics, Speech, and Signal Processing. 2000.

[Roweis, 2001] Roweis, S. T. *One Microphone Source Separation*. Neural Information Processing Systems (NIPS) 2000, pages 793-799 Edited by Leen, T. K., Dietterich, T. G., and Tresp, V. 2001. Denver, Colo., US, MIT Press.

[Schaub, 2008] Schaub, A. *Digital Hearing Aids*. Thieme Medical Publishers, 2008.

[Pedersen et al., 2008] Pedersen, M. S., Larsen, J., Kjems, U., and Parra, L. C. *A survey of convolutive blind source separation methods*, Benesty J, Sondhi M M, Huang Y (eds): Springer Handbook of Speech Processing, pp 1065-1094 Springer, 2008.

[Pedersen et al., 2006] Pedersen, M. S., Wang, D., Larsen, J., and Kjems, U. *Separating Underdetermined Convolutive Speech Mixtures*. ICA 2006. 2006.

The invention claimed is:

1. A hearing assistance system comprising
an input unit for providing electric input sound signals $u_i$, each representing sound signals $U_i$ from a multitude $n_u$ of sound sources $S_i$ (i=1, . . . , $n_u$),
an electroencephalography (EEG) system for recording activity of the auditory system of the user's brain and providing a multitude $n_y$ of EEG signals $y_j$ (j=1, . . . , $n_y$), and
a source selection processing unit coupled to said input unit and to said EEG-system and receiving said electric input sound signals $u_i$ and said EEG signals $y_j$, and in dependence thereof configured to provide a source selection signal $\hat{S}_x$ indicative of the sound source $S_x$ that the user currently pays attention to,
wherein
the source selection processing unit is configured to analyze said electric input sound signals $u_i$ i=1, . . . , $n_u$, and said multitude of EEG signals $y_j$, j=1, . . . , $n_y$,
using a selective algorithm that determines a sparse model to select the most relevant EEG electrodes and time intervals based on minimizing a cost function measuring the correlation between the individual sound source and the EEG signals, and
to determine a dynamic finite impulse response (FIR) filter from each sound source to each EEG channel using a full FIR single input multiple output (SIMO) model for each electric input sound signal $u_j$, based on said electric input sound signals $u_j$ and said EEG signals $y_j$, and
to use an alternating direction method of multipliers (ADMM) to provide sparse models from said full FIR single input multiple output (SIMO) models for use in identifying the model that best describes the corresponding electric input sound signal and EEG signal data, and
to determine the source selection signal $\hat{S}_x$ indicative of the sound source $S_x$ that the user currently pays attention to based on a cost function obtained for said multitude of sound sources by comparing cost functions of each model.

2. A hearing assistance system according to claim 1 wherein the source selection processing unit is configured to use a stimuli reconstruction (SR) method for estimating the FIR inverse model from EEG signal to sound source.

3. A hearing assistance system according to claim 2 wherein the source selection processing unit is configured to use a sparse model for modeling the finite impulse response (FIR) filter from each sound source to each EEG channel.

4. A hearing assistance system according to claim 2 wherein the source selection processing unit is configured to use the alternating direction method of multipliers (ADMM)

methodology to reformulate the optimization problem into another one with different B vectors in the cost function.

5. A hearing assistance system according to claim 1 wherein said input unit comprises a sound source separation unit for providing said electric input sound signals $u_i$ from one or more electric input sound signals representative of a mixture of said sound signals $U_i$.

6. A hearing assistance system according to claim 1 configured to provide an estimate $\hat{u}_x$ of the sound signal $U_x$ that the user currently pays attention to.

7. A hearing assistance system according to claim 1 wherein said EEG system comprises a multitude of EEG sensors, each comprising an EEG electrode, for providing said multitude of EEG signals $y_j$ (i=1, . . . , $n_y$).

8. A hearing assistance system according to claim 1 comprising one or two hearing devices, each hearing device being adapted for being located at or in an ear or for being fully or partially implanted in the head of a user, the or each hearing device comprising an output unit for providing output stimuli perceivable by the user as sound, based on said estimate $\hat{u}_x$ of the sound signal $U_x$ that the user currently pays attention to.

9. A hearing assistance system according to claim 8, wherein
said EEG system comprises a multitude of EEG sensors each comprising an EEG electrode, for providing said multitude of EEG signals, and
each hearing device comprises at least a part of said EEG system.

10. A hearing assistance system according to claim 8 wherein the hearing device or devices comprises a hearing aid, a headset, an earphone, an ear protection device, a speakerphone or a combination thereof.

11. A hearing assistance system according to claim 6 comprising first and second hearing devices, wherein the hearing assistance system is configured to allow the exchange of information between the first and second hearing devices or between the first and second hearing devices and an auxiliary device.

12. A hearing assistance system according to claim 11 configured to include electric input sound signals $u_{i,1}$ and $u_{i,2}$ provided by respective input units, and/or EEG signals $y_{j1,1}$ and $y_{j2,2}$ provided by respective EEG-systems of the first and second hearing devices in the determination of the sound source $S_x$ that the user currently pays attention to.

13. A hearing assistance system according to claim 8 comprising an auxiliary device configured to exchange information with the hearing device or with the first and second hearing devices.

14. A hearing assistance system according to claim 11 configured to maintain or apply appropriate directional cues for the electric sound signal $u_x$ representing the sound source $S_x$ that the user currently pays attention to.

15. A method of automatically selecting an audio source intended to be listened to by a wearer of a hearing device in a multi-audio source environment, the method comprising
providing electric input sound signals $u_i$, each representing sound signals $U_i$ from a multitude $n_u$ of sound sources $S_i$ (i=1, . . . , $n_u$),
recording activity of the auditory system of the user's brain and providing a multitude $n_y$ of EEG signals $y_j$ (j=1, . . . , $n_y$), and
providing a source selection signal $\hat{S}_x$ indicative of the sound source $S_x$ that the user currently pays attention to in dependence of said electric input sound signals $u_i$ and said EEG signals $y_j$, including
analyzing said electric input sound signals $u_i$ i=1, . . . , $n_u$, and said multitude of EEG signals $y_j$, j=1, . . . , $n_y$,
using a selective algorithm that determines a sparse model to select the most relevant EEG electrodes and time intervals based on minimizing a cost function measuring the correlation between the individual sound source and the EEG signals, and
to determine a dynamic finite impulse response (FIR) filter from each sound source to each EEG channel using a full FIR single input multiple output (SIMO) model for each electric input sound signal $u_i$, based on said electric input sound signals $u_i$ and said EEG signals $y_j$, and
to use an alternating direction method of multipliers (ADMM) to provide sparse models from said full FIR single input multiple output (SIMO) models for use in identifying the model that best describes the corresponding electric input sound signal and EEG signal data, and to
determine the source selection signal $\hat{S}_x$ indicative of the sound source $S_x$ that the user currently pays attention to based on cost functions obtained for said multitude of sound sources by comparing cost functions of each model.

16. A non-transitory computer readable medium storing a program comprising instructions which, when the program is executed by a computer, cause the computer to carry out the method of claim 15.

17. A data processing system comprising a processor and program code means for causing the processor to perform the method of claim 15.

* * * * *